United States Patent [19]

Evans et al.

[11] Patent Number: 5,639,592
[45] Date of Patent: Jun. 17, 1997

[54] FUNCTIONAL ANTAGONISM BETWEEN PROTO-ONCOPROTEIN C-JUN AND HORMONE RECEPTORS

[75] Inventors: Ronald M. Evans, La Jolla, Calif.; Ronald Schule, Schopfheim, Germany

[73] Assignee: The Salk Institute for Biological Studies, La Jolla, Calif.

[21] Appl. No.: 30,330

[22] PCT Filed: Sep. 20, 1991

[86] PCT No.: PCT/US91/06848

§ 371 Date: May 3, 1994

§ 102(e) Date: May 3, 1994

[87] PCT Pub. No.: WO92/05447

PCT Pub. Date: Apr. 2, 1992

Related U.S. Application Data

[63] Continuation-in-part of Ser. No. 586,187, Sep. 21, 1990, abandoned.

[51] Int. Cl.$^6$ .............................. G01N 33/53; C12Q 1/68; C12P 21/02; C12N 15/09; C12N 5/10
[52] U.S. Cl. .................................. 435/4; 435/6; 435/70.1; 435/172.3; 435/7.1; 435/375
[58] Field of Search .......................... 435/4, 6, 7.1, 69.1, 435/70.1, 71.1, 172.3, 240.2

[56] References Cited

PUBLICATIONS

Doucas et al. (1991) "Unregulated expression of c Jun or c–Fos proteins but not JunD inhibits ostrogen receptor activity in human breast cancer derived cells." EMBO J 10:2237–2245.
Lucibello et al (1990) "Mutual transrepression of Fos and the gluco corticoid receptor: involvement of a Functional domain in Fos which is absent in FosB" EMBO J 9:2827–2834.
Angel et al (1987) "Phorbol ester–inducible genes contain a common cis element recognized by a TPA–modulated transacting factor", Cell 49: 729–739.
Schüle et al. (1991) Cross–compling of signal transduction pathways: zinc finger meats leucine zipper. Trends in Genetics 7:377–381.
Sassone–Corsi et al., "Direct interaction betwen fos and jun nuclear oncoproteins: role of the 'leucine zipper' domain" Nature 336:692–695 (1988).
Schüle et al., "Jun–Fos and Receptors for Vitamins A and D Recognize a Common Response Element in the Human Osteocalcin Gene" Cell 61:497–504 (1990).
Schüle et al., "Functional Antagonism between Oncoprotein c–Jun and the Glucocorticoid Receptor" Cell 62:1217–1226 (1990).

Schüle et al., "Retinoic acid is a negative regulator of AP–1–responsive genes" Proc. Natl. Acad. Sci. USA 88:6092–6096 (1991).
Diamond et al., "Transcription Factor Interactions: Selectors of Positive or Negative Regulation from a Single DNA Element" Science 249:1266–1272 (1990).
Jonat et al., "Antitumor Promotion and Antiinflammation: Down–Modulation of AP–1 (Fos/Jun) Activity by Glucocorticoid Hormone" Cell 62:1189–1204 (1990).
Kouzarides and Ziff, "The role of the leucine zipper in the fos–jun interaction" Nature 336:646–651 (1988).
Kruijer et al., "Platelet–derived growth factor induces rapid but transient expression of the c–fos gene and protein" Nature 312:711–716 (1994).
Lamph, William W., "Cross–Coupling of AP–1 and Intracellular Hormone Receptors" Cancer Cells 3(5):183–185 (1991).
Landschulz et al., "The Leucine Zipper: A Hypothetical Structure Common to a New Class of DNA Binding Proteins" Science 240:1759–1764 (1988).
Mitchell et al., "Rapid Induction of the Expression of Proto–oncogene fos during Human Monocytic Differentiation" Cell 40:209–217 (1985).
Mordacq and Linzer, "Co–localization of elements required for phorbol ester stimulation and glucocorticoid repression of proliferin gene expression" Genes & Development 3:760–769 (1989).
Ransone and Verma, "Nuclear Proto–Oncogenes Fos and Jun" Ann. Rev. Cell Biol. 6:539–557 (1990).
Ryder et al., "A gene activated by growth factors is related to the oncogene v–jun" Proc. Natl. Acad. Sci. USA 85:1487–1491 (1988).

Primary Examiner—Jasemine C. Chambers
Assistant Examiner—Scott D. Priebe
Attorney, Agent, or Firm—Gray Cary Ware & Freidenrich; Stephen E. Reiter

[57] ABSTRACT

Hormone receptors and the transcription factor Jun/AP–1 have been shown to reciprocally repress one another by a mechanism which is independent of DNA binding. For example, over-expression of AP–1 represses glucocorticoid-induced activation of genes carrying a functional glucocorticoid response element. Conversely, glucocorticoid has been shown to repress the transcriptional activation of genes which are controlled by promoters which contain the AP–1 binding site. In addition, methods are disclosed for selecting compounds useful for treating cells undergoing uncontrolled proliferation, such compounds being capable of disrupting the function of AP-1, but display substantially no ability to promote the transcriptional activation of hormone responsive genes.

22 Claims, 14 Drawing Sheets

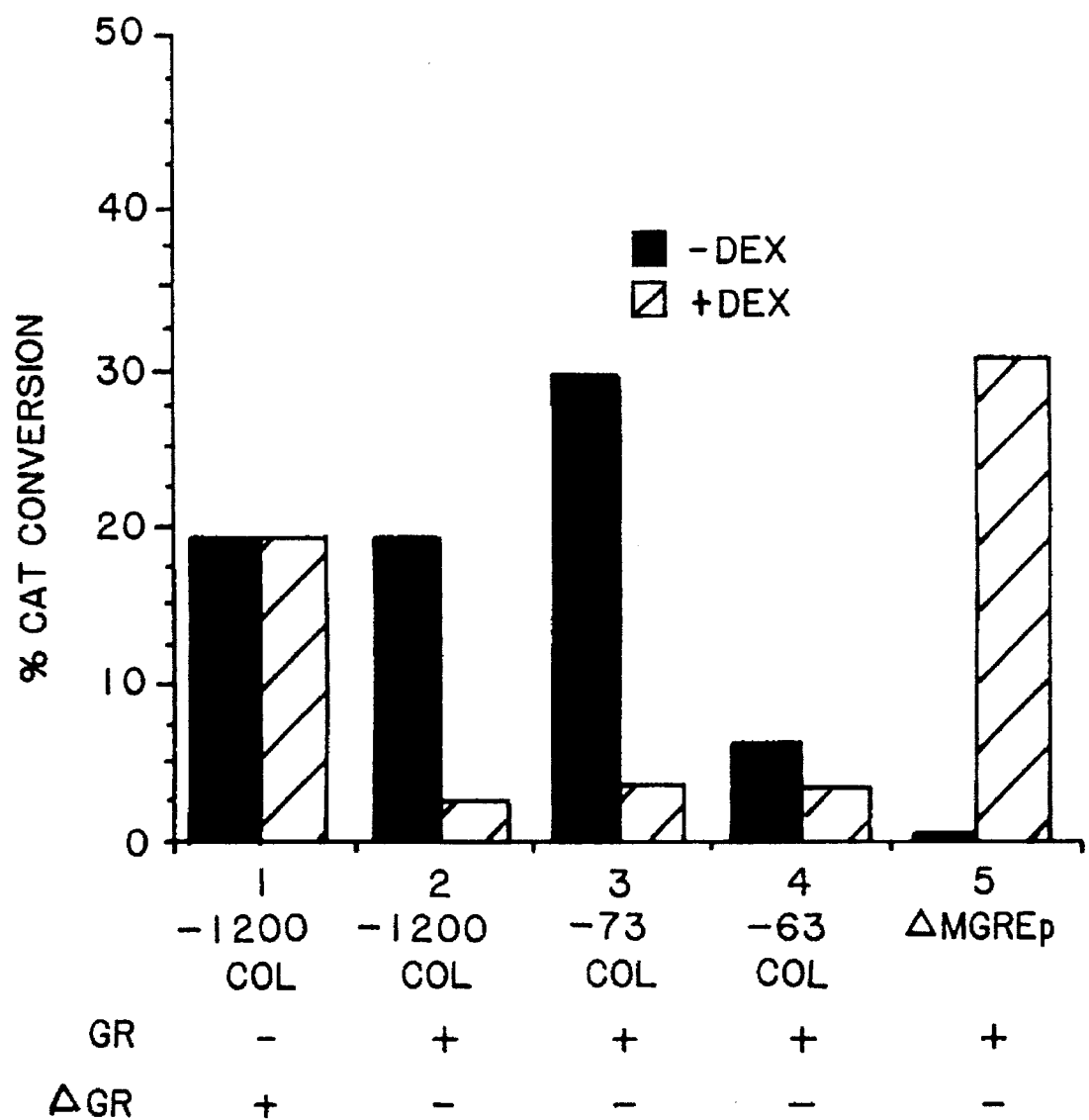

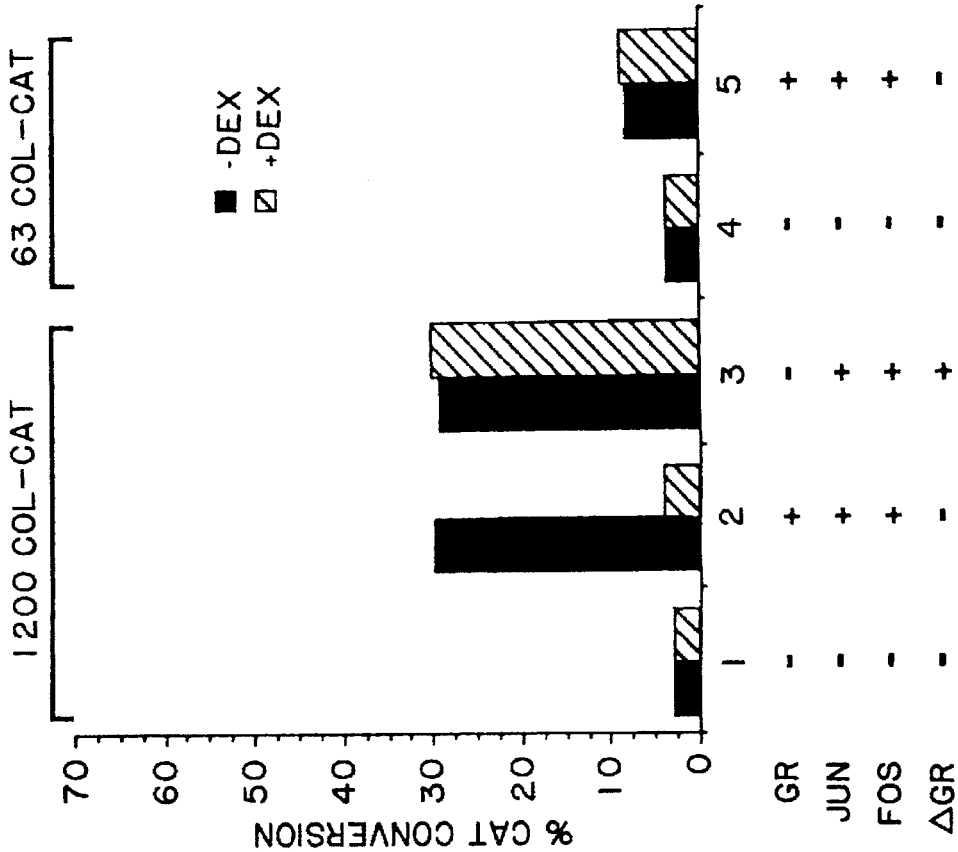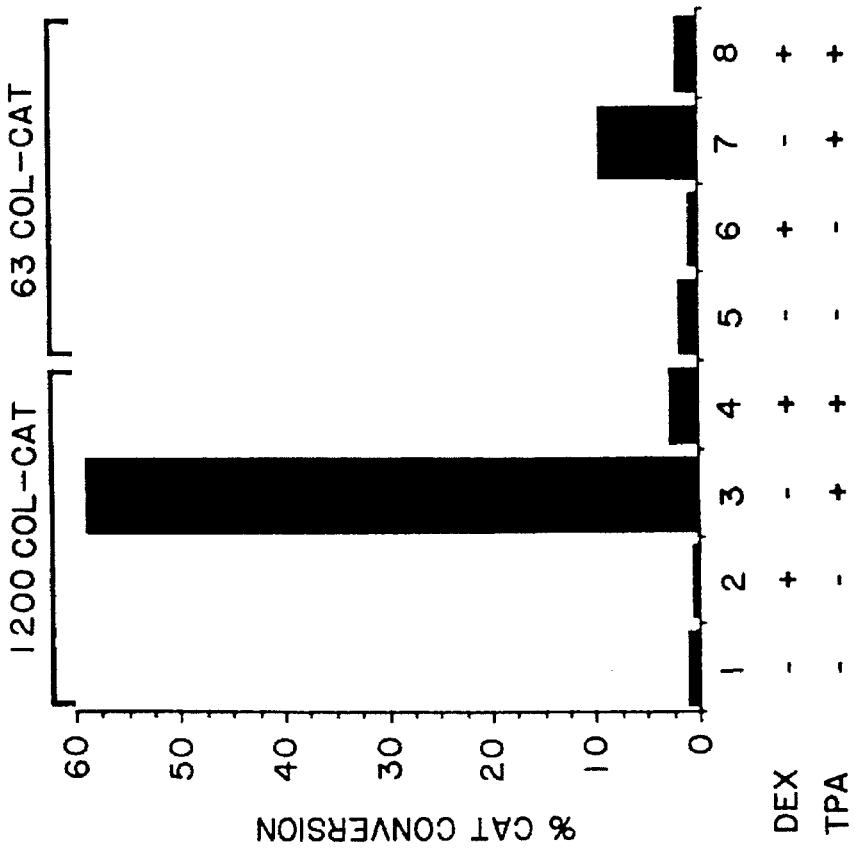

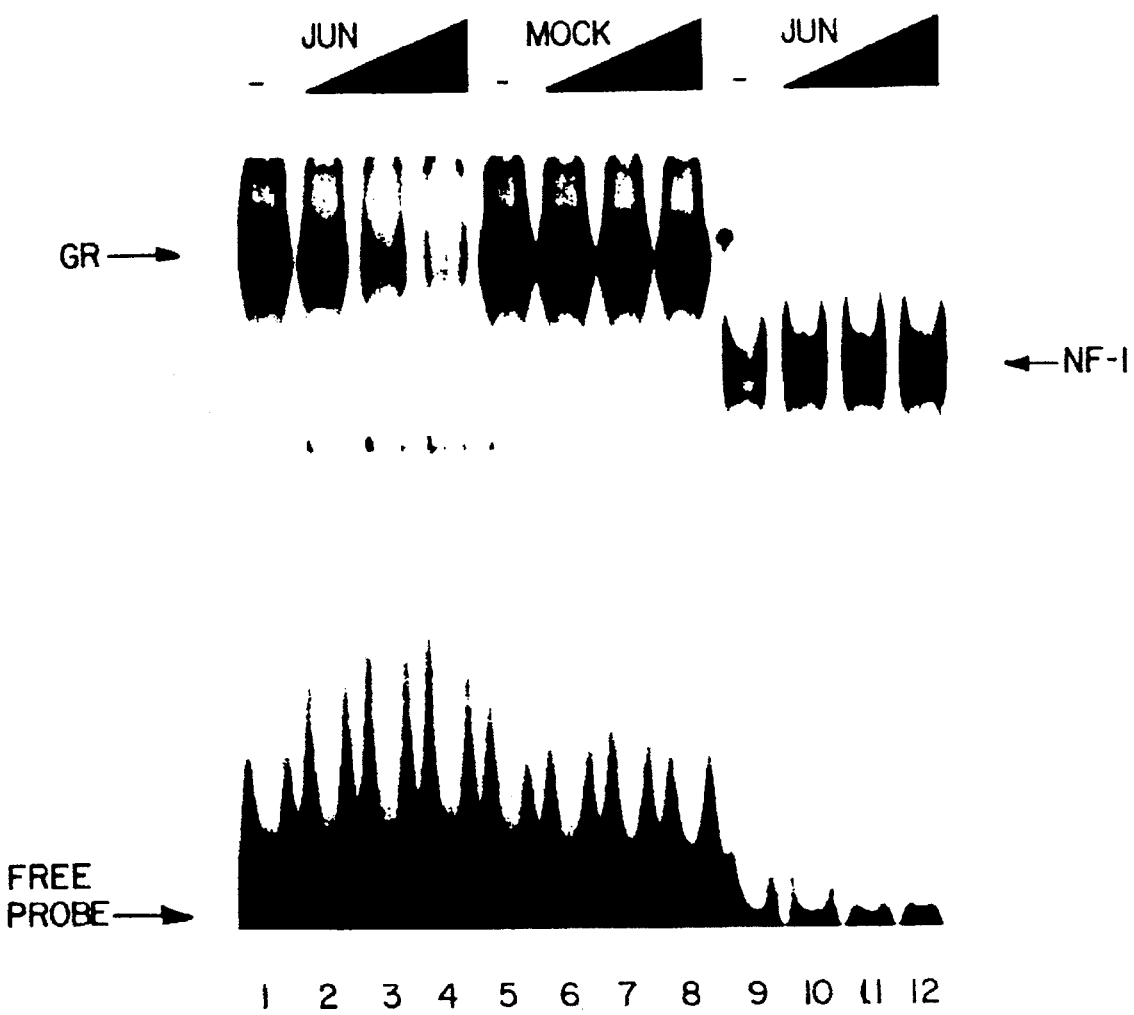

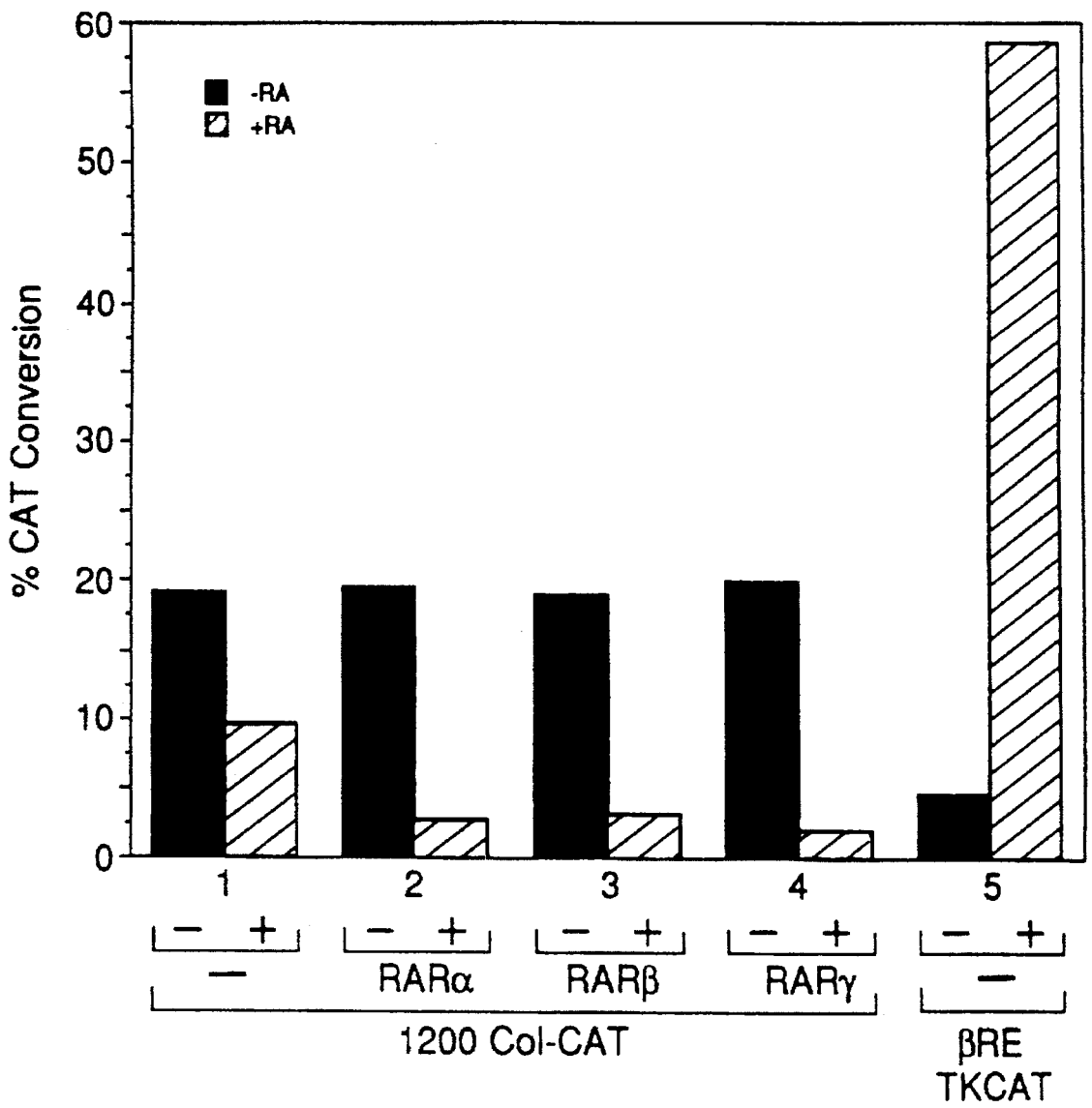

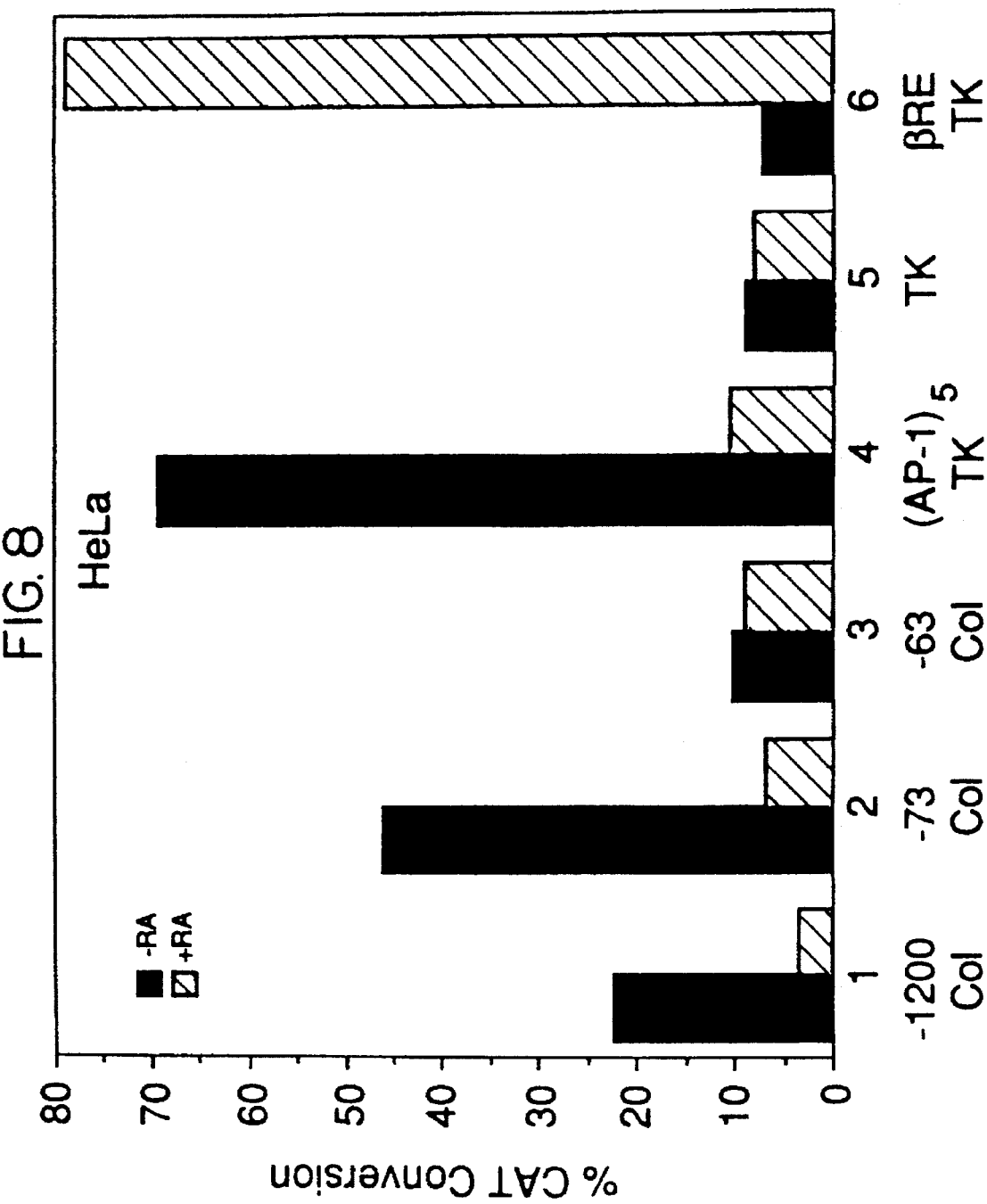

FIG. 9

| | | Repression of (AP-1)$_5$-TKCAT | |
|---|---|---|---|
| | | −RA | +RA |
| 1. RAR | [1—81 R | 153 R | 462 R] | <1 | 100 |
| 2. Δ1-81 | [81 R | 153 R | 462] | <1 | 92 |
| 3. Δ81-153 | [1—81 R | 153 R | 462] | <1 | <1 |
| 4. RGR | [1—81 R | 153 G | 462 R] | <1 | 100 |
| 5. 403* | [1—81 R | 153 R | 403* R] | <1 | <1 |
| 6. 203* | [1—81 R | 153 R | 203*] | <1 | <1 |
| 7. RRerbA | [1—81 R | 153 R | 361 erbA 639] | <1 | <1 |
| 8. RXRα | [1 RXRα 462] | <1 | <1 |

FUNCTIONAL ANTAGONISM BETWEEN PROTO-ONCOPROTEIN C-JUN AND HORMONE RECEPTORS

This application is a 371 application of PCT/US91/06848, filed Sep. 20, 1991 and a continuation-in-part of application Ser. No. 07/586,187, filed Sep. 21, 1990, now abandoned.

This invention was made with Government support under grant GM26444, awarded by the National Institute of Health. The Government has certain rights in the invention.

This invention relates to steroid hormones, steroid hormone-like compounds, steroid hormone receptors, steroid hormone-like receptors, and related species. In a particular aspect, this invention relates to processes mediated by steroids and related hormones. In a further aspect, this invention relates to processes mediated by the proto-oncogenic protein complex, AP-1.

BACKGROUND OF THE INVENTION

Steroids and related hormones play an important role in regulating development, differentiation and homeostasis. The hormones exert their regulatory effects by binding to a superfamily of intracellular receptors, which are direct modulators of gene transcription. Mutational analyses of hormone receptors have identified functional domains responsible for transcriptional activation, nuclear localization, DNA binding, and hormone binding.

Hormone receptors can act to both activate transcription, and to repress expression of a variety of genes. It has been postulated that such repression is mediated by binding of the hormone receptor to DNA regulatory sequences, termed negative hormone response elements, thereby displacing transcriptional activators.

It would be desirable to be able to control the degree to which hormones, either directly or indirectly, activate transactivation and/or the degree to which hormones, either directly or indirectly, repress the expression of certain genes, for such purposes as the treatment of disease states, the development of treating agents with reduced incidence of side effects, and so forth.

The AP-1 protein complex is a member of a class of nuclear proteins encoded by proto-oncogenes that have been implicated in diverse aspects of cell growth, differentiation, and development. The AP-1 binding site is recognized by c-Jun homodimers and c-Jun/c-Fos heterodimers. Binding of c-Fos to the AP-1 site is dependent on the formation of heterodimers with c-Jun. Homodimer and heterodimer formation is mediated through non-covalent interactions facilitated by a structure termed the leucine zipper. In addition to imparting positive regulatory effects on several pathways, the AP-1 complex has also been shown to confer negative regulation on several genes.

Up until now, the effect of a given protein on gene regulation has generally been thought to be the result of interaction between the protein and a regulatory element within the promoter region of the gene being regulated. Thus, compounds which exert an effect on more than one pathway are thought to recognize a responsive element which is common to more than one pathway. Consistent with this, Diamond et al., [in Science 249: 1266–1272 (1990)] describe studies employing a "composite" glucocorticoid response element (GRE), which binds selectively in vitro to both glucocorticoid receptor and c-Jun and c-Fos (components of the phorbol ester-activated AP-1 transcription factor). The authors then propose a general model for composite GRE action that requires DNA binding for interaction between receptor (i.e., glucocorticoid receptor) and non-receptor factors (i.e., c-Jun or c-Fos).

Based on the above-described understanding of the mechanism by which regulatory proteins exert their effects, it would not be possible to alter one regulatory effect of a given protein without also altering some other regulatory effects of that protein. Thus, for any beneficial effect achieved by administration of a hormone or hormone analog, there is a strong likelihood that an undesirable side effect will occur, i.e., promotion of undesired processes and/or inhibition of desired processes. Accordingly, there has been no motivation in the art to search for compounds which are capable of disrupting a known pathway without also undesirably impacting other regulatory pathways.

SUMMARY OF THE INVENTION

In accordance with the present invention, we have discovered that hormone receptors and transcription factor, AP-1, can reciprocally repress each other's transcriptional activation activity. Similarly, we have discovered that hormone receptors and transcription factor, AP-1, can reciprocally derepress each other's ability to inhibit expression of certain genes. This is believed to occur via a novel mechanism which is independent of DNA binding.

The present invention, therefore, provides means to control the transcription activation of hormone-responsive gene products, and/or AP-1 responsive gene products. In addition, the present invention provides means to screen for compounds that inhibit cell growth, but which do not promote differentiation of said cells.

BRIEF DESCRIPTION OF THE FIGURES

FIG. 2A, FIG. 2B and FIG. 2C show the repression of the collagenase promoter by the glucocorticoid receptor.

FIG. 3A and FIG. 3B show the repression of an AP-1-induced collagenase promoter-CAT reporter by the glucocorticoid receptor.

FIG. 6A, FIG. 6B and FIG. 6C present gel retardation assays performed to investigate the ability of c-Jun to repress the binding of the glucocorticoid receptor to a glucocorticoid response element.

FIG. 7 shows the repression of RAR-mediated repression of collagenase promoter activity.

FIG. 8 shows the repression of the collagenase promoter by the retinoic acid receptor-alpha.

FIG. 9 summarizes the results of a deletion study to determine domains of the retinoic acid receptor which repress AP-1 induced expression by the collagenase promoter.

DETAILED DESCRIPTION OF THE INVENTION

Figure 1B:
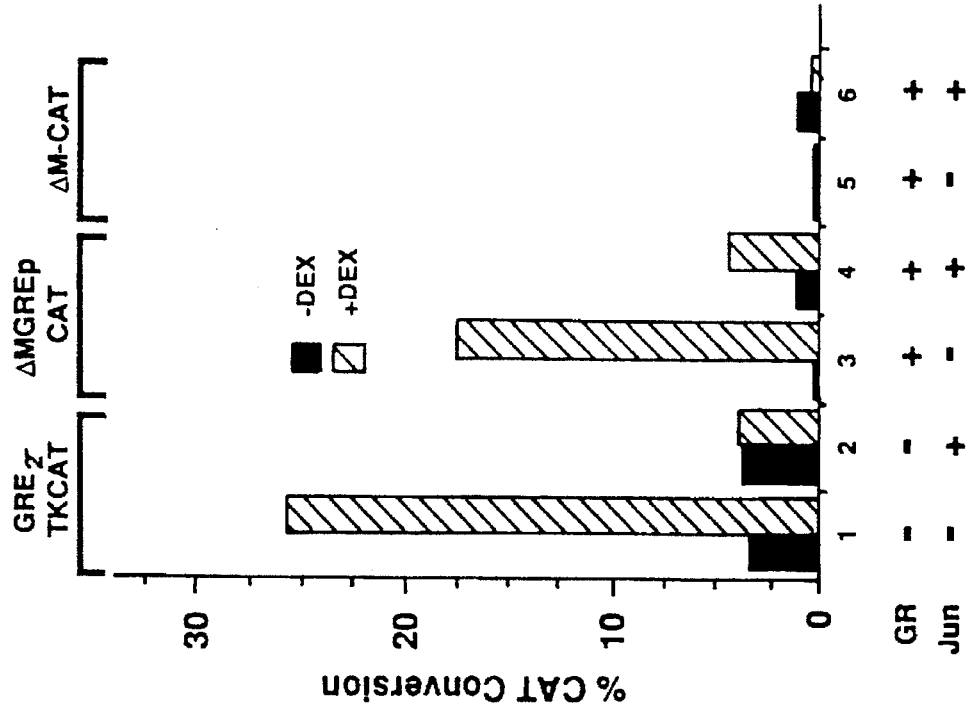
FIG. 1A and FIG. 1B show the repression of glucocorticoid-mediated induction of transcription by the transcription factor c-Jun.

In accordance with the present invention, there is provided a method for identifying compound(s) useful for treating abnormal cells, said method comprising selecting a compound which displays both:
(a) the ability to disrupt the function of AP-1, when said compound is employed in a first assay system comprising a cell line capable of expressing:
  (i) steroid hormone or steroid hormone-like receptor,
  (ii) AP-1, and
  (iii) AP-1-responsive reporter; and
(b) substantially no ability to promote the transcriptional activation of steroid hormone-responsive or steroid hormone-like responsive genes, when said compound is employed in a second assay system comprising a cell line capable of expressing:
  (i) steroid hormone or steroid hormone-like receptor, and
  (ii) steroid hormone- or steroid hormone-like responsive reporter.

In accordance with another embodiment of the present invention, there is provided a method for identifying compound(s) which disrupt the AP-1 response pathway, but which exert substantially no effect on steroid hormone or steroid hormone-like responsive pathways, said method comprising:
(a) testing said compound in a first assay system to determine the effect of said compound on the AP-1 responsive pathway; wherein said first assay system comprises a cell line capable of expressing:
  (i) steroid hormone or steroid hormone-like receptor,
  (ii) AP-1, and
  (iii) AP-1-responsive reporter, and
(b) testing said compound in a second assay system to determine the effect of said compound on the transcriptional activation of steroid hormone or steroid hormone-like responsive genes; wherein said second assay system comprises a cell line capable of expressing:
  (i) steroid hormone or steroid hormone-like receptor, and
  (ii) steroid hormone-responsive or steroid hormone-like-responsive reporter; and thereafter
selecting those compounds which have an inhibitory effect in the testing of part (a), and substantially no effect in the testing of part (b).

In accordance with a further embodiment of the present invention, there is provided a method to repress, in an expression system, transcription activation of steroid hormone-responsive or steroid hormone-like-responsive gene(s) by steroid hormones or steroid hormone-like compound(s), said method comprising:

exposing said system to compound(s) and/or condition(s) which induce AP-1 expression, effective to repress expression of said steroid hormone-responsive or steroid hormone-like-responsive gene(s).

It is desirable that the expression systems employed in this embodiment of the present invention be responsive to steroid hormone or steroid hormone-like compounds, while at the same time being substantially non-responsive to the presence of c-Jun, c-Fos, or AP-1.

In accordance with yet another embodiment of the present invention, there is provided a method to repress, in an expression system, transcription activation of steroid hormone-responsive or steroid hormone-like-responsive gene(s) by steroid hormone or steroid hormone-like compound(s), or analogs thereof, said method comprising:

administering to said system a peptide comprising the leucine zipper region of c-Jun, or a functional analog thereof, in an amount effective to repress expression of said steroid hormone-responsive or steroid hormone-like-responsive gene(s).

As with the preceding embodiment of the present invention, it is desirable for the expression systems employed in this embodiment of the present invention to be responsive to steroid hormone or steroid hormone-like compounds, while being substantially non-responsive to the presence of c-Jun, c-Fos, or AP-1.

In accordance with still another embodiment of the present invention, there is provided a method to repress, in an expression system, transcription activation of AP-1-responsive gene(s) by AP-1, or analogs thereof, said method comprising:

administering to said system a composition comprising:
  (i) functional ligand-binding domain of steroid hormone receptor or steroid hormone-like receptor, or analog thereof, and
  (ii) functional DNA-binding domain of steroid or steroid-like receptor, or analogs thereof,
in an amount effective to repress expression of said AP-1-responsive gene(s).

It is desirable that the expression systems employed in this embodiment of the present invention be responsive to c-Jun, c-Fos, or AP-1, while being substantially non-responsive to the presence of steroid hormone or steroid hormone-like compounds.

In accordance with a still further embodiment of the present invention, there is provided a method to overcome, in the presence of asteroid hormone or steroid hormone-like compound, or analog thereof, the repression of expression of gene product(s) from genes subject to negative regulation by steroid hormone receptors, steroid hormone-like receptors or analogs thereof, said method comprising:

exposing said system to compound(s) and/or condition(s) which induce AP-1 expression, in an amount effective to suppress the repression of expression of said gene product(s).

In accordance with a further embodiment of the present invention, there is provided a method to overcome the inhibition of proliferation and function of lymphoid cells by asteroid hormone, steroid hormone-like compound, or analog thereof, in the presence of asteroid hormone receptor or steroid hormone-like receptor, or analog thereof, said method comprising:

exposing said system to compound(s) and/or condition(s) which induce AP-1 expression, effective to suppress the inhibition of proliferation and function of said lymphoid cells.

In accordance with a still further embodiment of the present invention, there is provided a compound which forms a first complex with asteroid hormone or steroid hormone-like receptor; wherein said first complex, in the presence of AP-1, disrupts the function of AP-1; and wherein said first complex is substantially unable to promote transcriptional activation of steroid hormone or steroid hormone-like responsive genes.

Hormone-mediated transcription activation has been elucidated for many hormones; and for some hormones, this mode of activation can effect many different genes. It is sometimes desirable to modulate this transcription activation. In accordance with the present invention, this can be accomplished by either exposing the system to compound(s) and/or condition(s) which induce AP-1 expression, or by administering to the system a peptide comprising the leucine zipper region of c-Jun, or analogs thereof, in an amount effective to repress expression of the hormone responsive gene product.

Compounds which are capable of inducing the expression of AP-1 include compounds which induce tumor formation (e.g., phorbol esters), growth factors (e.g., EGF, FGF, CSF), cytokines (e.g., IL-1, IL-2), neuropeptides (e.g., somatostatin), neurotransmitters (e.g., acetylcholine), protein kinase c (and compounds capable of inducing protein kinase c, e.g., EGF, insulin, platelet-derived growth factor, alpha-1 andronergic agents, IL-1, IL-2, and the like), and the like.

Conditions which are capable of inducing the expression of AP-1 include exposure of the system to ultraviolet irradiation, gamma irradiation, heat shock, stress, and the like.

Alternatively, instead of inducing the expression of endogenous (or exogenous) AP-1, the invention process can be accomplished by administering effective amounts of the c-Jun leucine zipper region to the system. Administration of a peptide comprising this component can be accomplished in a variety or ways, e.g., by direct introduction of purified or semi-purified peptide composition containing the desired component; by inducing expression of a gene construct encoding the leucine zipper region; and the like.

The leucine zipper region is a fragment of at least 29 amino acids, which orient themselves in an alpha-helix, wherein each seventh amino acid of the amino acid chain is a leucine, so that the leucine residues of one alpha-helix can interdigitate with the leucine residues of a second alpha-helix, e.g., another c-Jun moiety, (thereby producing homodimer), a c-Fos moiety (thereby producing heterodimer), and the like.

The molar ratio of protein comprising the c-Jun leucine zipper region, relative to the molar amount of steroid hormone receptor present in the expression system can vary widely. Broadly, ratios in the range of about 0.5 up to 100:1 are useful. Preferably, ratios of AP-1 component (or derivatives thereof) to steroid hormone receptor will fall in the range of about 1 up to 20:1; with molar ratios in the range of about 5 up to 15:1 being the presently most preferred ratio.

Steroid hormone or steroid hormone-like responsive genes contemplated for use in this embodiment of the present invention include glucocorticoid-responsive gene(s), retinoic acid-responsive gene(s), vitamin R-responsive gene (s), thyroid hormone responsive gene(s), mineralocorticoid-responsive gene(s), estrogen-responsive gene(s), estrogen-related hormone-responsive gene(s), androgen-responsive gene(s), progesterone-responsive gene(s), retinoid-responsive gene(s), arylhydrocarbon-responsive gene(s), and the like.

The invention method for the modulation of hormone induced transcription activation can be employed to treat a subject displaying a disease state. Disease states which are amenable to such treatment include anorexia nervosa, alcoholism, severe depression, chronic stress syndrome (which diseases are associated with suppression of the immune system caused by abnormally high levels of glucocorticoids), and the like.

Hormones are also known to exert negative regulation on certain processes. It is sometimes desirable to modulate this negative regulation. In accordance with the present invention, this can be accomplished by either exposing the system to compound(s) and/or condition(s) which induce AP-1 expression, or by administering to said system a peptide comprising the leucine zipper region of c-Jun, or analogs thereof, in an amount effective to suppress the hormone-mediated repression of expression of gene products.

Genes subject to negative regulation by steroid hormones or steroid hormone-like compounds include the pro-opiomelanocortin gene, the prolactin gene, the proliferin gene, the chorionic gonadotropin alpha-subunit gene, the phosphoenolpyruvate carboxykinase gene, and/or the collagenase gene.

AP-1-mediated transcription activation has also been elucidated for numerous gene products. It is sometimes desirable to modulate this transcription activation. In accordance with the present invention, this can be accomplished by administering to the AP-1-responsive system a composition comprising:

(i) functional steroid hormone receptor or steroid hormone-like receptor ligand-binding domain, or analog thereof, and (ii) functional steroid hormone receptor or steroid hormone-like receptor DNA-binding domain, or analog thereof, in an amount effective to repress expression of gene products.

The composition employed in this embodiment of the present invention can be administered as a single protein containing both the ligand-binding domain and the DNA binding domain, or as two separate proteins, each providing one of the desired functions. It is presently preferred, for ease of handling, that the two desired functions be provided as part of a single protein.

Regardless of whether the composition employed in this embodiment of the invention is administered as one or two protein species, the composition can be introduced into the system to be modulated in a variety of ways. For example, purified or semi-purified protein(s) can be administered directly to the system. Alternatively, expression vector(s) encoding the desired protein(s) can be induced to express such products.

The molar ratio of composition comprising the ligand binding domain and DNA binding domain, relative to AP-1 present in the expression system, can vary widely. Broadly, ratios in the range of about 0.5 up to 100:1 are useful. Preferably, ratios of composition to AP-1 will fall in the range of about 1 up to 20:1; with molar ratios in the range of about 5 up to 15:1 being the presently most preferred.

The method of the invention can be employed in a variety of ways, e.g., for treating disease states which are stimulated by AP-1. Such disease states include tumor formation (e.g., formation of lymphomas), arthritis, asthma, allergies, rashes, and the like.

Hormone receptors contemplated for use in the practice of the present invention include the intracellular steroid receptors, such as, for example, glucocorticoid receptor(s), retinoic acid receptor(s), vitamin $D_3$ receptor(s), thyroid receptor(s), mineralocorticoid receptor(s), estrogen receptor (s), estrogen-related receptor(s), retinoid receptor(s), androgen receptor(s), progesterone receptor(s), arylhydrocarbon receptor(s) and the like. Presently preferred receptors include glucocorticoid receptor(s), thyroid receptor(s), mineralocorticoid receptor(s), estrogen receptor(s), estrogen-related receptor(s), retinoid receptor(s), androgen receptor (s) and progesterone receptor(s). The presently most preferred receptor for use in the practice of the present invention is the glucocorticoid receptor, because this receptor has been particularly thoroughly characterized.

In accordance with one embodiment of the present invention, a compound useful for treating abnormal cells can be identified by screening for compounds which meet the two criteria of disrupting the function of AP-1, but which fail to promote transcriptional activation of steroid hormone-responsive genes.

A convenient means to assess the ability of test compound to disrupt the function of AP-1 is to employ the test compound in an assay system comprising a cell line capable of expressing steroid hormone receptor, AP-1, and AP-1-responsive reporter. Cells which express endogenous receptor, AP-1 and AP-1-responsive reporter, or cells having an exogenous source of one or more of the above can be employed. Preferred cells to employ for this purpose are cells which do not have a "hormone response element" associated with the AP-1 responsive reporter.

If the compound is effective in disrupting the function of the AP-1 pathway, the AP-1 responsive reporter (a gene product which can be readily measured by conventional methods) will not be expressed. Conversely, if the compound fails to disrupt the AP-1 responsive pathway, the AP-1 responsive reporter will be expressed and can readily be measured.

A convenient means to assess the ability of test compound to promote (or fail to promote) transcriptional activation of steroid hormone responsive genes, is to employ the test compound in an assay system comprising a cell line capable of expressing a hormone receptor and a hormone-responsive reporter. Cells expressing endogenous steroid hormone receptor and/or steroid hormone-responsive reporter can be employed. Alternatively, cells transfected with an exogenous source of steroid hormone receptor and/or steroid hormone-responsive reporter can be employed. If the test compound promotes transcriptional activation, the steroid hormone-responsive reporter will be expressed, and can readily be measured. Conversely, if the test compound does not promote transcriptional activation, the steroid hormone-responsive reporter will not be expressed.

The invention will now be described in greater detail by reference to the following non-limiting examples.

EXAMPLES

Experimental procedures employed in the examples described herein are set forth below:
Recombinant Plasmids The collagenase-CAT constructs and plasmid (AP-1)$_5$-TKCAT have been described by Angel et al., (See *Mol. Cell. Biol.*, 1: 2256–2266 (1987).

The recombinant GR mutants have been described by Hollenberg et al., (See *Cell*, 49: 39–46 (1987) and *Cell* 55: 899–906 (1988)), Giguere et al., *Nature* 330: 624–629 (1987), and Umosono and Evans *Cell* 57: 1139–1146 (1989).

The RAR mutant RARα∆1-80 was generated by replacing the NotI-BamHI fragment of GR13 with that of RAR$_{NX}$ [see Hollenberg and Evans in *Cell* 86: 899–906 (1988)]. Mutant RARα∆$_{NX}$ was generated by replacing the NotI-XhoI fragment of RARα$_{NX}$ with a synthetic oligonucleotide containing NotI-XhoI restriction sites.

The recombinant mouse c-Jun constructs have described by Lamph et al., *Nature* 334: 629–631 (1988) and Ransone et al., (See *Genes and Devel.* 3: 770–781 (1989) and *Proc. Nat'l Acad. Sci. U.S.A.* 87: 3806–3810 (1990)). Construct SVTLZJun was created by amplification of DNA sequences coding for amino acids 282 to 334 of mouse c-Jun (Lamph et al., supra) by polymerase chain reaction and subsequent ligation downstream of a SV40 nuclear translocation signal (Kalderon et al., *Cell* 39: 499–509 (1984) in a pRS expression vector (Giguere et al., *Cell* 46: 645–652 (1986). The sequence was confirmed according to Taboe and Richardson, *Proc. Nat'l. Acad. Sci. U.S.A.* 84: 4767–4771 (1987).

Transfections and Reporter Assays

Transfection of plasmid DNA into HeLa, NIH3T3, or CV-1 cells was performed using the standard calcium phosphate co-precipitation technique described by Gorman et al., in *Mol. Cell. Biol.* 2: 1044–1051 (1982) with minor modifications described by Schüle et al., in *Nature* 332: 87–90 (1988). Cells were maintained in DMEM medium supplemented with 10% bovine calf serum (BCS). Twenty-four hours before transfection, 7×10$^5$ cells/100 mm dish were plated in phenol-red free DMEM supplemented with 10% charcoal-treated bovine calf serum (BCS). Typically 2 µg of reporter plasmid and 2 µg of an RAS-β-galactosidase (internal control for transfection efficiently) expression plasmids (Umesono and Evans, supra) were used. Co-transfection of additional expression constructs is indicated in each example. The total amount of transfected DNA was always adjusted to 20 µg with pUC18. The cells were exposed to the precipitate for 16–20 hours. Unless otherwise indicated, the cells were refed with phenol-red free DMEM, 10% charcoal-treated BCS and 10$^{-7}$M DEX (or 10$^{-6}$M RA) was added. For TPA induction of Col-CAT reporter constructs, HeLa cells were refed with phenol-red free DMEM supplemented with 0.5% charcoal-treated BCS and incubated simultaneously with 100 ng/ml TPA and 10$^{-7}$M DEX.

Protein-DNA Binding Assays

Three µl of freshly in vitro-translated proteins were pre-incubated in binding buffer [10 mM HEPES, pH 7.8/4 mM MgCl$_2$/0.1 mM EDTA/4 mM spermidine/2 mM dithiothreitol, bovine serum albumin at 100 µg/ml/poly(dI-dC) at 1 µg/ml/15% (vol/vol) glycerol] on ice for ten minutes. Subsequently, 2 ng of $^{32}$P-labeled oligonucleotide probes (4×10$^4$ dpm) was added to the reaction mixture. For the competition assay, various amounts of bacterially expressed GR, RARα or untransformed bacterial BL-21 lysate were added simultaneously with Jun proteins. Jun proteins were either translated in vitro or obtained from HeLa cell extracts. After additional incubation on ice for 15 minutes, the protein-DNA complexes were resolved by 4% PAGE in 45 mM Tris/32.3 mM boric acid/1.25 mM EDTA, pH 8.3. The dried gel was then exposed with intensifying screen at −70° C. with Kodak XAR film.

EXAMPLE 1

Jun Represses GR Mediated Activation c-Jun and GR expression plasmids were co-transfected into NIH3T3 cells and assayed to see whether c-Jun was able to inhibit GR-mediated activation of a GRE$_2$-TKCAT reporter plasmid [Schüle et al., *Science* 242: 1418–1420 (1988)]. NIH3T3 cells were used in this experiment because they contain endogenous GR and upon starvation express only residual amounts of the AP-1 complex. As shown in FIG. 1, GR strongly induced reporter activity upon the addition of the synthetic glucocorticoid dexamethasone.

Figure 1A:
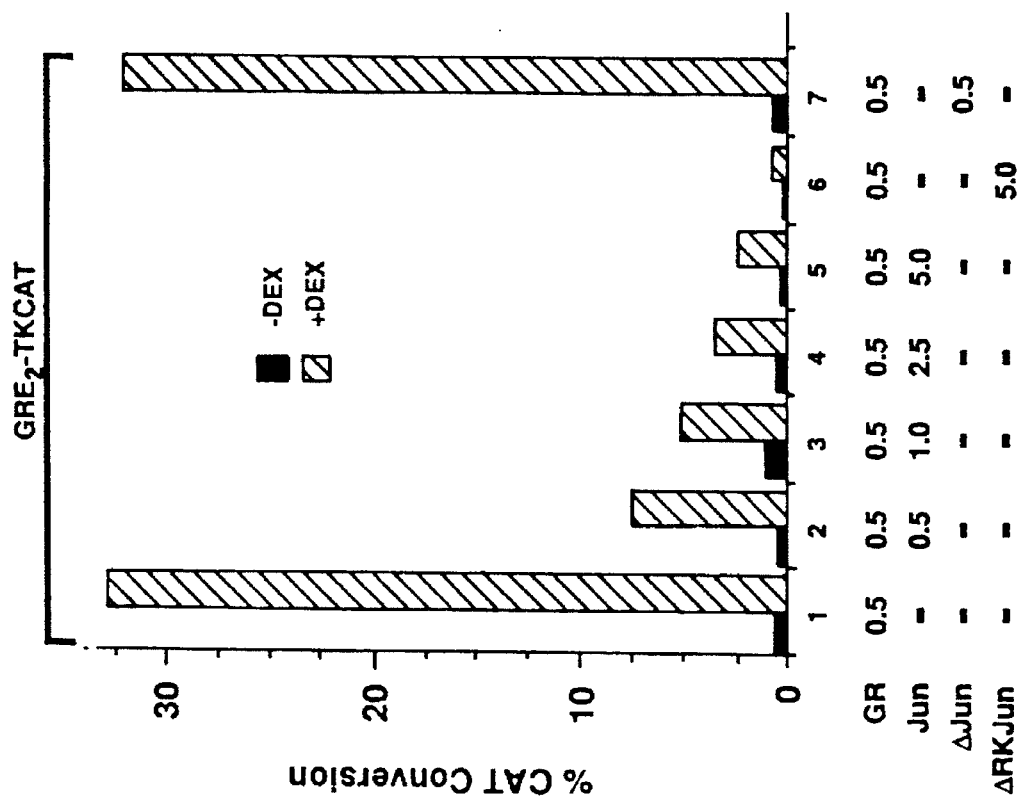

Co-transfection was carried out with constant amounts of GR plasmid expression and various amounts of c-Jun expression plasmid, ∆Jun, a construct lacking the c-Jun coding sequences and ∆RKJun, a construct lacking the c-Jun DNA binding domain, were also included in the Experiment. In FIG. 1, the cells are shown as either untreated (black bars) or treated with DEX (striped bars). Numbers presented in the Figure indicate g of co-transfected plasmid DNA. As shown in FIG. 1A, GR strongly induced reporter activity upon the addition of the synthetic glucocorticoid dexamethasone (DEX) (FIG. 1A, lane 1). Co-transfection of increasing amounts of c-Jun expression plasmids inhibited hormone-induced reporter activity in a concentration-dependent manner (FIG. 1A, compare lanes 1 with 2–5). In contrast, transfection of parental plasmid ΔJun, which lacks c-Jun coding sequences, did not alter the activity of $GRE_2$-TKCAT (FIG. 1A, lane 7). Because the $GRE_2$-TKCAT reporter lacks an intrinsic AP-1 site, inhibition does not appear to require binding of c-Jun to DNA. This was corroborated by a mutant, ΔRKJun lacking a functional DNA binding domain, (FIG. 1A, lane 6). This mutant produced levels of repression similar to that of the wild-type c-Jun protein (FIG. 1A, compare lanes 5 and 6). The expression of control plasmid TKCAT, lacking the GRE, was not influenced by either hormone treatment or over-expression of c-Jun. c-Jun also repressed the hormone dependent activation of $GRE_2$-TKCAT by endogenous GR present in NIH3T3 cells (FIG. 1B, compare lanes 1 AND 2).

To further demonstrate that c-Jun mediated repression is not specific for a particular GRE or promoter sequence, we transfected $ΔMGRE_p$-CAT reporter plasmid (Thompson and Evans, Proc. Nat'l. Acad. Sci. U.S.A. 86: 3494–3498 (1989) containing a palindromic GRE in the mouse mammary tumor virus promoter was transfected into NIH3T3 cells. Transcriptional activity of $GRE_2$-TKCAT, $ΔMGRE_p$-CAT and the control plasmid AM-CAT in NIH3T3 cells in the absence (black bars) or presence (striped bars) of DEX is shown in FIG. 1B. Transcriptional activity was analyzed with endogenous receptor activity present in NIH3T3 cells (lanes 1–2) or in cells transfected with 0.5 µg of GR expression plasmids (lanes 3–6). Where indicated (+)5 µg of C-Jun expression plasmids were co-transfected. The NIH3T3 cells were cultured in low (0.5%) serum. The activity of this construct was efficiently induced by GR in the presence of hormone (FIG. 1B, lane 3) and repressed by over-expression of c-Jun (FIG. 1B, lane 4). Neither hormone treatment nor over-expression of c-Jun significantly altered activity of the control plasmid ΔM-CAT (FIG. 1B, lanes 5 and 6).

EXAMPLE 2

The Collagenase AP-1 Site Is Required for DEX Repression

Figure 2A:
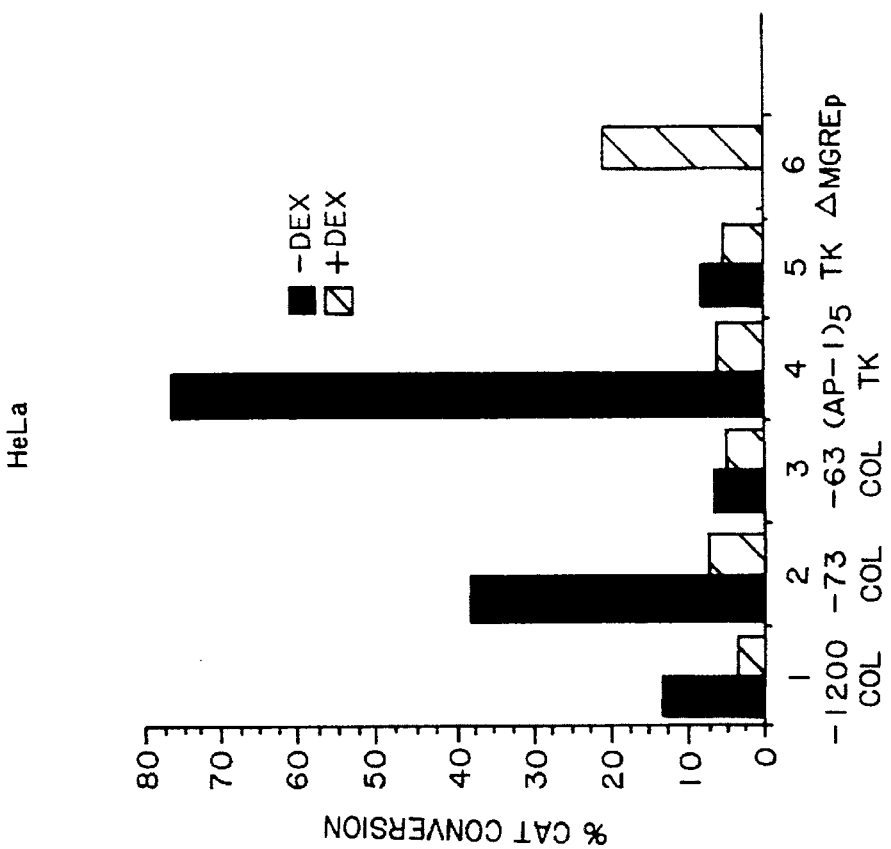

In this example, the ability of the GR to inhibit induction of an AP-1 responsive promoter was examined. The AP-1 inducible reporter construct $(AP-1)_5$-TKCAT was transfected into GR negative CV-1 cells cultured in low (0.5%) serum (FIG. 2A). FIG. 2A summarizes the activity of reporter construct $(AP-1)_5$-TKCAT and the control plasmid TKCAT in untreated (shown as black bars) or DEX treated (shown as striped bars) CV-1 cells co-transfected with either GR expression plasmid or parental vector ΔGR lacking the GR coding sequences, and Jun/Fos expression plasmids. The CV-1 cells were cultured in low (0.5%) serum. This promoter has a high basal activity which is further stimulated (FIG. 2A, lane 2) by the cotransfection of Jun/Fos expression vectors. The presence of DEX and GR leads to potent inhibition of this induction (lane 2), whereas the control plasmid ΔGR, lacking the GR coding sequences, has no effect on Jun/Fos induction in the presence of DEX (lane 3). As shown with the TKCAT control (lanes 4 and 5), induction is dependent on the presence of the AP-1 sites and, in the absence of these sites, glucocorticoids alone have no effect.

Figure 2B:
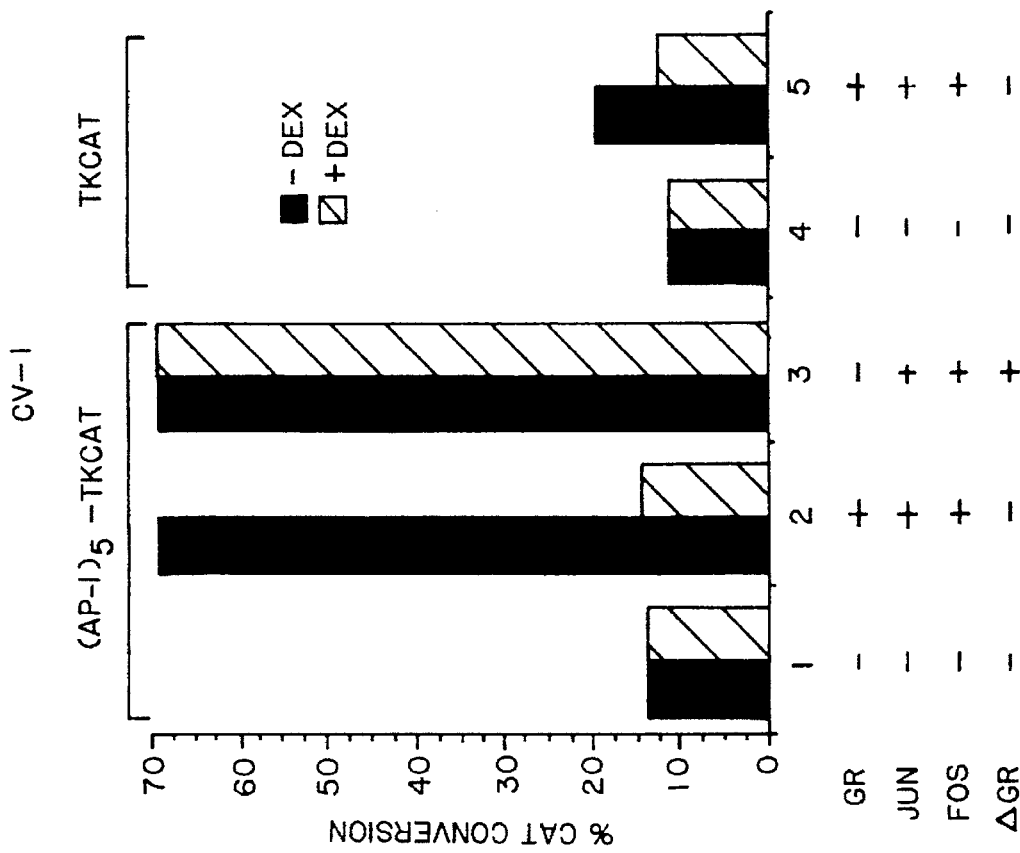

The collagenase promoter provided an opportunity to examine this potential regulation of a cellular gene by GR. This gene was chosen because glucocorticoids have been shown to negatively regulate its expression [See Brinckerhoff et al., Biochemistry 25: 6378–6384 (1988)]. Whereas Jun/AP-1 and factors stimulating the Jun/AP-1 pathway are known to positively induce its activity, various collagenase promoter-CAT reporter plasmids were transfected into HeLa or CV-1 cells, respectively. HeLa and CV-1 cells were used because collagenase is expressed in both cell lines [Angel et al., Mol. Cell. Biol. 7: 2256–2266 (1987)]. In addition, HeLa cells express endogenous GR activity. FIG. 2B shows transcriptional activity of various collagenase promoter-CAT deletion mutants and heterologous reporters in HeLa cells cultured in 10% serum in the absence (black bar) or presence of DEX (striped bar). In the Figure, "TK" refers to the thymidine kinase-CAT construct; "$(AP-1)_5$TK" refers to a construct comprising five copies of the collagenase AP-1 site in front of TK-CAT; and "$ΔMGRE_p$" refers to a construct comprising a consensus GRE cloned into DMCAT. As shown in FIG. 2B (lanes 1–3) addition of DEX to HeLa cells resulted in a 4–5 fold repression of 1200 Col-CAT and 73 Col-CAT reporter activity respectively, whereas the activity of the reporter plasmid 63 Col-CAT remained unchanged. These results indicate that repression is mediated by DNA sequences located between position −73 and −63 in the collagenase promoter. This region has been shown to contain a TPA-inducible enhancer which is recognized by AP-1 complex. The DEX responsive reporter $ΔMGRE_p$-CAT was activated in a hormone-dependent manner, indicating that the repression of the collagenase promoter or a heterologous reporter is dependent on the presence of the AP-1 site (FIG. 2B, lanes 6).

To demonstrate that repression is not cell-type specific, GR expression vector was co-transfected together with the Col-CAT reporter plasmids into GR-negative CV-1 cells. FIG. 2C shows transcriptional activity of collagenase promoter deletion mutants and $ΔMGRE_p$-CAT in CV-1 cells cultured in 10% serum and co-transfected with either GR expression plasmid or the control plasmid (ΔGR) in the absence (black bar), or presence of DEX (striped bar). Lane 1 of FIG. 2C shows that addition of DEX to CV-1 cells transfected with parental plasmids lacking the coding sequence for GR did not alter Col-CAT activity. In contrast, in the presence of the receptor, 1200 Col-CAT and 73 Col-Cat were potently repressed in a hormone dependent manner (FIG. 2C, lanes 2–3) while 63 Col-CAT was only slightly affected by the activated GR (FIG. 2C, lane 4).

To further explore the interaction between GR and Jun/AP-1, Col-CAT reporter activity was increased by either treatment with TPA or, alternatively, by over-expressing the Jun and Fos proteins. Expression of Collagenase-CAT deletion mutants was measured in untreated HeLa cells incubated with either TPA, DEX, or a combination of both. Transcriptional activity of Collagenase-CAT deletion mutants was measured in untreated (black bars) or DEX-treated (striped bars) CV-1 cells co-transfected with either GR expression plasmid, parental vector ΔGR lacking the GR coding sequences, or Jun/Fos expression plasmids. Both HeLa and CV-1 cells were cultured in low (0.5%) serum. As shown in FIG. 3A, addition of TPA to HeLa cells cultured in low (0.5%) serum strongly elevates 1200 Col-CAT activity (compare lanes 1 and 3). This induction was severely reduced by the stimulation of endogenous GR receptors by DEX addition (FIG. 3A, lane 4). Expression of 63 Col-CAT was only weakly affected by either treatment (FIG. 3A, lanes 5–8). Expression of 1200 Col-CAT can be elevated by co-transfecting Jun/Fos expression plasmids into CV-1 cells cultured in low (0.5%) serum (FIG. 3B, lane 2). These induced levels were efficiently repressed by DEX-activated GR (FIG. 3B, compare lanes 1 and 2). No repression was seen when the parental plasmid ΔGR lacking the GR coding sequences, was used (FIG. 3B, lane 3). Neither hormone treatment nor over-expression of Jun/Fos altered activity of the control plasmid 63 Col-CAT significantly (FIG. 3B, lanes 4 and 5).

The data shown in FIGS. 2 and 3 demonstrate that both activation and repression of the collagenase promoter and the TK reporter is dependent on the presence of transcriptional activity of the AP-1 site. The AP-1 site is the major enhancer in the promoter of the collagenase gene and the only enhancer of $(AP_{-1})_5$-TKCAT. Thus, glucocorticoids may function as general modulators of AP-1 responsive genes.

EXAMPLE 3

Figure 4:
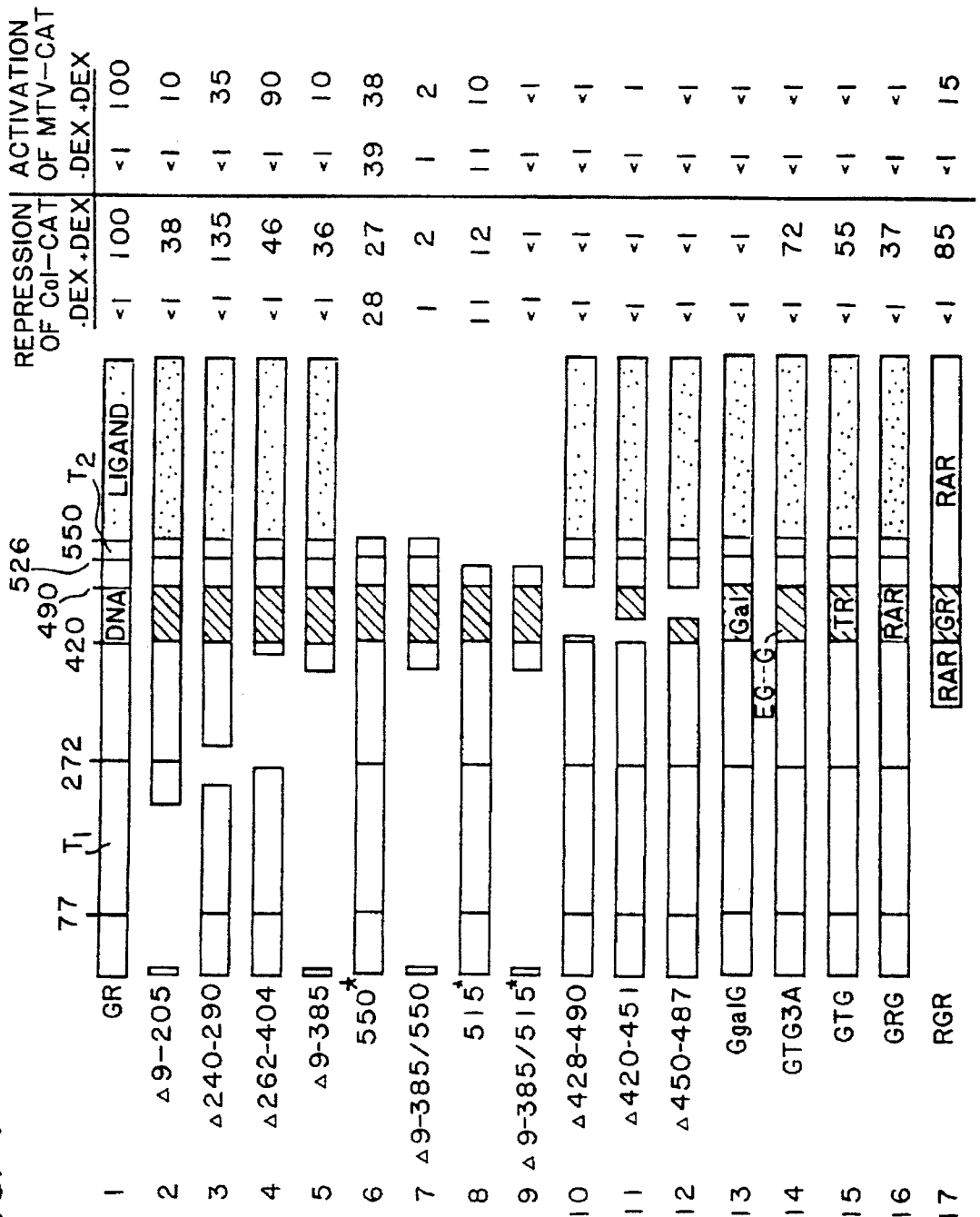
FIG. 4 summarizes the results of a deletion study to determine domains of the glucocorticoid receptor which repress AP-1 induced expression and induce glucocorticoid-mediated transcription.

GR DNA Binding Domain Is Necessary But Not Sufficient for Repression of Jun/AP-1 Activity The above experiments demonstrate that Jun/AP-1 activation can be efficiently repressed by GR in a hormone dependent manner. To define regions of the receptor involved in repression, several GR mutants were analyzed in co-transfection studies in CV-1 cells for their ability to repress 1200 Col-CAT reporter activity. In FIG. 4, GR mutants previously characterized for transcriptional activation, nuclear localization, DNA binding, and ligand binding were assayed for their ability to repress activity of the 1200 Col-CAT reporter or to activate the MTV-CAT reporter. The wild-type receptor consists of two activation domains (τ1 and τ2), the DNA binding domain (DNA) and a ligand binding domain (ligand). In FIG. 4, the scale above the depicted mutants indicates amino acid position numbers. The deleted amino acids are indicated on the left. In some mutants, the GR DNA binding domain is replaced by the DNA binding domains of GAL4 (GgalG), TR (GTG), or RAR (GRG). The recombinant mutant RGR is composed of the GR DNA binding domain plus RAR amino- and carboxy-termini. The mutant GTG3A contains three point mutations (EG—G) in the P-box of the GR DNA binding domain. Repression of 1200 Col-CAT reporter activity obtained with wild-type GR was set at 100%. All mutants were expressed in similar amounts in the cell as assayed by Western blot analysis. The hybrid receptors shown in rows 13–17 activate their cognate response elements in a hormone-dependent manner. Most amino-terminal deletion mutants exhibited reduced glucocorticoid-mediated repression (FIG. 4, compare lane 1 with lanes 2–5). Interestingly mutant Δ240-290 (lane 3), which has a short deletion in a transcriptional activation domain, termed $τ_1$, repressed reporter activity better than wild-type GR. The carboxy-terminal truncation mutants 550* and 515* both exhibited markedly reduced hormone independent repression activity (lane 6 and 8). These data show that the ligand binding domain and, to a lesser extent, the amino terminus contribute to repressor activity.

Deletion of the entire DNA binding domain resulted in a complete loss of repression (lane 10, mutant Δ428-490). Further analysis revealed that deletion of either the first zinc finger (lane 11, mutant Δ420-451) or the second zinc finger (lane 12, mutant Δ450-487) of the GR completely eliminated repression. Although the DNA binding domain is necessary for repression, it is not sufficient, since mutants expressing only this region (lane 7, mutant Δ9-385/550* and lane 9, mutant Δ9-385/515*) are also inactive. Substitution of the GR DNA binding domain for that of the yeast transcription factor GAL4 resulted in a mutant which failed to repress (lane 13, mutant GgalG), even though it is able to activate GAL4 responsive promoters in a hormone-dependent fashion. The importance of the GR DNA binding domain is unexpected because GR does not bind to the collagenase AP-1 site (as shown in FIG. 6).

To provide further evidence that DNA binding is not necessary for GR-mediated repression (in contrast to the requirement for DNA binding in order for the interaction observed by Diamond et al., supra, to occur), a mutant receptor having a changed target gene specificity was examined to ascertain if it had lost the ability to repress. This GR mutant, which was generated through point mutations in the P-box of the DNA binding domain, recognizes TRE or ERE instead of the GRE. This mutant is still able to repress with only slightly reduced efficiency (FIG. 4, lane 14). In similar experiments, mutants in which the GR DNA binding domain had been swapped with those of either the RAR or TR (mutants GRG and GTG), were capable of repressing 1200 Col-CAT expression (FIG. 4A, lanes 15 and 16). Finally, a mutant (RGR) in which the GR amino- and carboxy-termini had been exchanged with that of RAR also repressed efficiently (lane 17).

Together these results indicate that the GR DNA binding domain and an intact finger structure are required for efficient repression. However, the target gene specificity of the DNA binding domain does not appear to be important, as substitution of the DNA binding domains of several steroid hormone receptors for that of the GR did not abolish the repression activity. In addition, a mutant receptor which consists of RAR amino- and carboxy termini and the GR DNA binding domain still retained repression activity.

EXAMPLE 4

The c-Jun Leucine Zipper Is Required for Repression of GR Activity

To determine which region of the c-Jun protein is responsible for repression of GR-mediated activation, a series of mutant c-Jun proteins were tested in NIH3T3 cells cultured in low (0.5%) serum for their ability to repress $GRE_2$-TKCAT activity. $GRE_2$-TKCAT or TKCAT reporter constructs were co-transfected into NIH3T3 cells with 0.5 μg GR expression plasmid with or without 5 μg of one of the indicated mutants. The cells were cultured in low (0.5%) serum.

Figure 5:
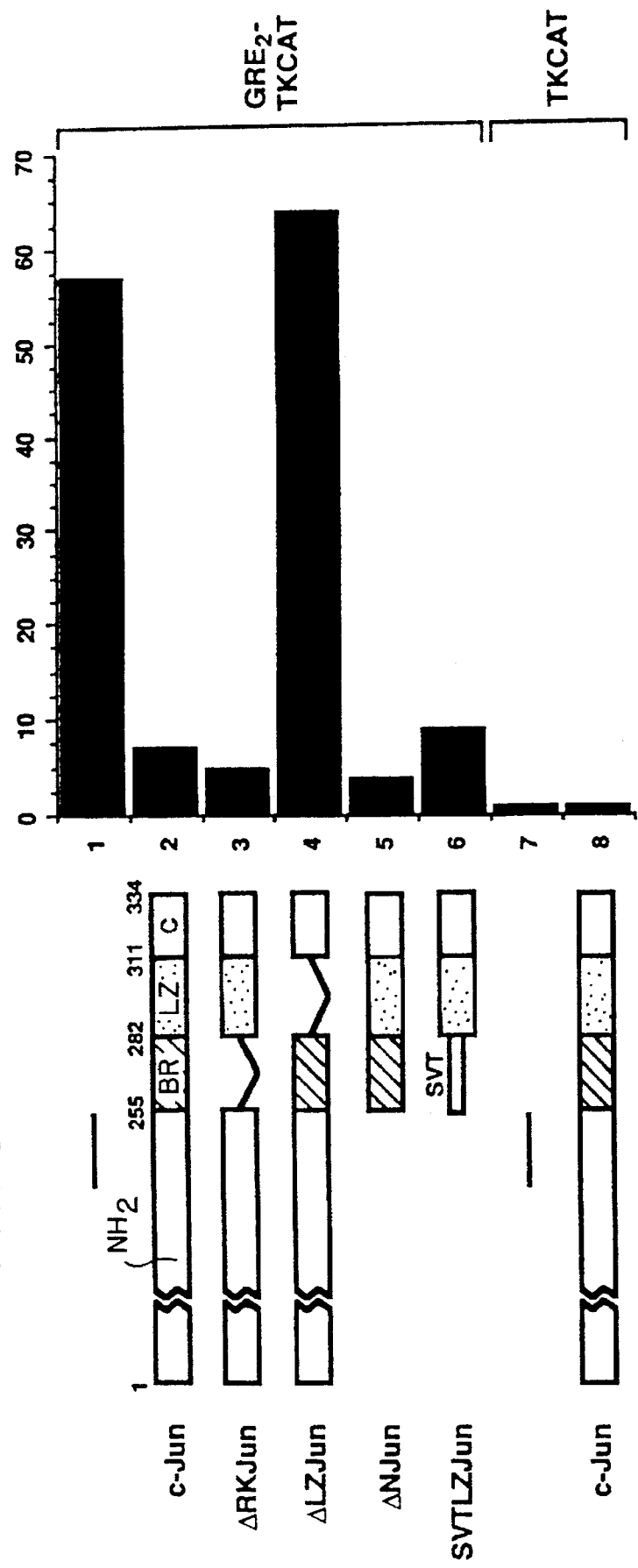
FIG. 5 presents a deletion analysis of the c-Jun gene, with an indication of the ability of the various deletion mutants to repress glucocorticoid-mediated transcription activation.

FIG. 5 shows reporter activity as fold induction. The c-Jun protein is depicted as consisting of an amino terminus ($NH_2$), a DNA binding region (BR), a leucine zipper (LZ), and a carboxy terminus (C). The numbers above the depicted mutants indicate positions of amino acids at the start or end of the corresponding region. The mutant SVTLZJun contains an SV40 nuclear translocation signal cloned in front of the leucine zipper. The c-Jun mutants were expressed in similar amounts. Deletion of either the c-Jun DNA binding domain (FIG. 5, lane 3) or the entire amino terminus (FIG. 5, lane 5) did not alter the ability of the c-Jun protein to repress $GRE_2$-TKCAT reporter activity. Deletion of the leucine zipper, however, abolished the protein's ability to repress (FIG. 5, lane 4).

To further examine the ability of the c-Jun leucine zipper to repress GR-mediated activation, a mutant was constructed which fused the leucine zipper plus 23 carboxy-terminal amino acids to a SV40 nuclear localization signal. As shown in FIG. 5, lane 6, this mutant repressed reporter activity at levels similar to wild-type c-Jun. Activity of control plasmid TKCAT was not altered by either hormone treatment or over-expression of c-Jun (FIG. 5, lanes 7 and 8).

The results shown in FIGS. 4 and 5 demonstrate that c-Jun is able to efficiently repress GR-mediated activation and that the carboxy-terminal region of c-Jun containing the leucine zipper is sufficient for this effect.

EXAMPLE 5

Inhibits GR-GRE Complex Formation

Figure 6A:
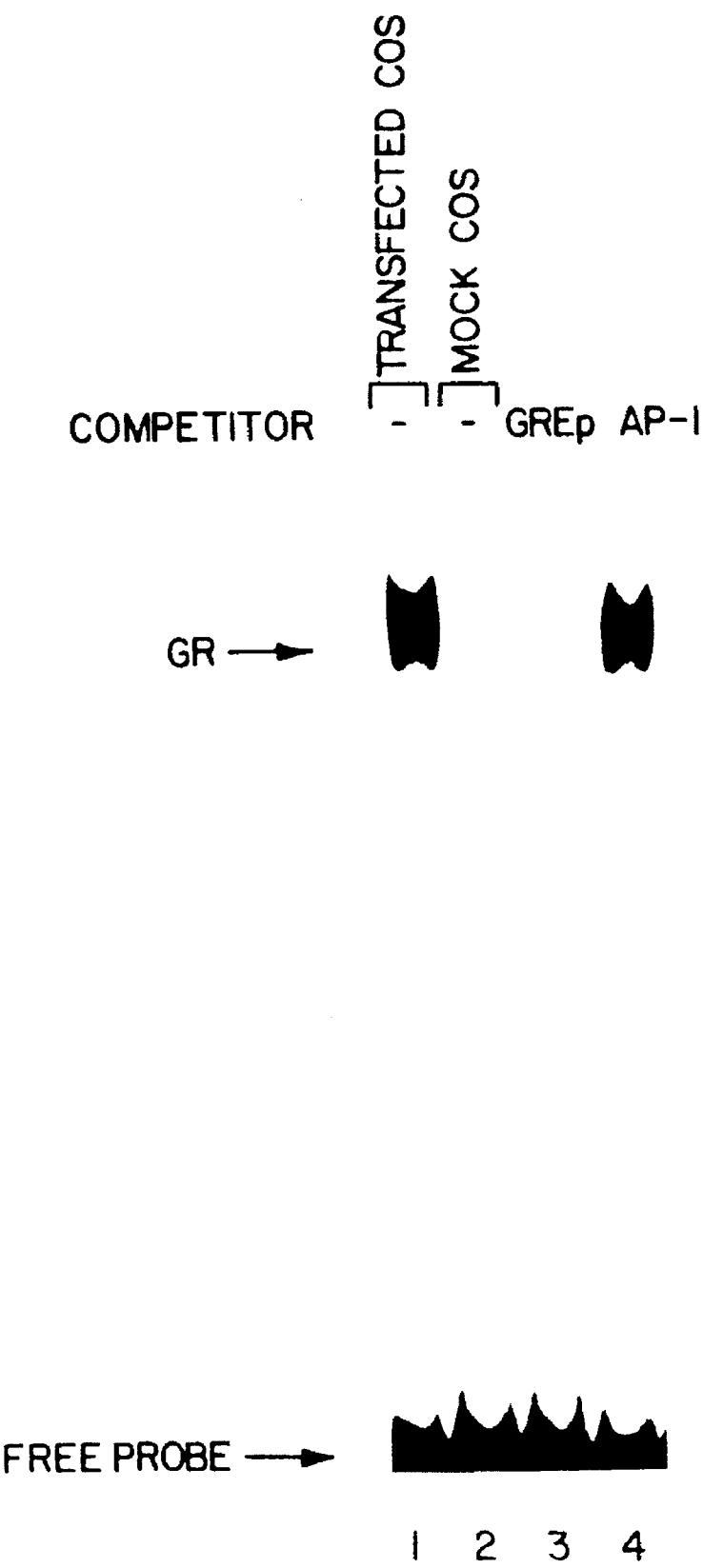

To test for a potential physical interaction between c-Jun and GR, gel retardation assays were performed. These assays were performed with $^{32}$P-labeled oligonucleotide containing a palindromic GRE and extracts prepared from COS cells transfected with constructs expressing either GR (FIG. 6A, lanes 1, 3, and 4) or beta-galactosidase (FIG. 6A, lane 2). Competition reactions were performed using a 50-fold excess of unlabeled oligonucleotide containing the $GRE_p$ (FIG. 6A, lane 3) or the collagenase AP-1 binding site (FIG. 6A, lane 4).

GR (obtained by over-expression in COS cells) formed a specific, retarded complex with an oligonucleotide containing a palindromic GRE (FIG. 6A, lane 1). The GR-GRE complex, while efficiently competed by a 50-fold excess of unlabeled GRE (lane 3), was unaffected by competition with a 50-fold excess of an oligonucleotide containing the AP-1 site found in the collagenase promoter (lane 4). This result indicates that the GR does not bind to the collagenase AP-1 binding site.

Gel retardation assays were performed with $^{32}$P-labeled oligonucleotides containing a palindromic GRE (FIG. 6B, lanes 1–8) or an NF-1 binding site (FIG. 6B, lanes 9–12) and extracts prepared from COS cells expressing the GR. Reactions were done in the absence (FIG. 6B, lanes 1, 5, and 9) or in the presence of 63 ng (FIG. 6B, lanes 2, 6, and 10), 130 ng (FIG. 6B, lanes 3, 7, and 11), or 250 ng (FIG. 6B, lanes 4, 8, and 12) of purified, bacterially-expressed c-Jun (FIG. 6B, lanes 1–4 and 9–12) or BL21 bacterial lysates (Mock) lanes 5–8).

Addition of increasing amounts of purified, bacterially expressed c-Jun is seen to result in a severe reduction in the amount of GR-GRE complex formed (FIG. 6B, lanes 2–4). In contrast, addition of mock-transformed bacterial lysate did not affect GR-GRE complex formation (FIG. 6B, lanes 5–8).

To demonstrate the specificity of the effect of c-Jun on GR-GRE interactions, gel retardation assays were performed using COS cell extracts (containing GR) and an oligonucleotide containing an NF-1 binding site. Addition of increasing amounts of c-Jun had no effect on NF-1 binding activity (FIG. 6B, lanes 9–12).

To further correlate these in vitro data with the in vivo results, a c-Jun truncation mutant, termed ΔNJun, (see FIG. 5, lane 5) was assayed for its ability to disrupt GR-GRE interactions. ΔNJun, which has amino acids 1–249 deleted, retains the leucine zipper and basic domains of the c-Jun protein. Consistent with in vivo results, the truncation mutant was capable of disrupting formation of the GR-GRE complex (FIG. 6C; wherein gel retardation assays were performed with a $^{32}$P-labeled oligonucleotide containing a palindromic GRE and extracts prepared from COS cells which express the GR). Reactions were done in the absence (lanes 1 and 5) or presence of 200 ng (lanes 2 and 6), 400 ng (lanes 3 and 7), or 800 ng (lanes 4 and 8) of purified, bacterially-expressed mutant ΔNJun (lanes 1–4) or BL21 bacterial lysates (Mock; lanes 5–8).

EXAMPLE 6

RAR Mediated Repression of Collagenase Promoter Activity

A reporter plasmid containing a 1.2-kilobase portion of the collagenase promoter fused to the bacterial chloamphenicol acetyltransferase (CAT) gene (1200Col-CAT) was co-transfected into HeLa cells along with 0.1 µg of expression plasmids coding for RARα, RARβ and RARγ (FIG. 7, bars 2–4), cultured in 10% serum and assayed to see whether the reporter gene is influenced by retinoic acid (RA). HeLa cells were used in this experiment because they contain endogenous RAR and express the collagenase gene as well as Jun protein. As shown in FIG. 7, endogenous RAR repressed 1200Col-CAT activity by about 50% upon RA addition (FIG. 7, bars 1). Co-transfection of any one of RARα, RARβ or RARγ expression plasmids further inhibited 1200Col-CAT reporter activity to about 15% of the non-RA treated controls (FIG. 7, bars 2–4). In contrast, the control plasmid βRE-TKCAT (which contains a known RA-response element, βRARE [see Sucov et al., in Proc. Natl. Acad. Sci. USA 87: 5392–5396 (1990)]) was induced by RA, indicating that RA-mediated repression is specific for the collagenase promoter (FIG. 7, bars 5).

EXAMPLE 7

The AP-1 Site in the Collagenase Promoter Is Required for RA-Mediated Repression In this example, those DNA sequences in the collagenase promoter (i.e., an AP-1 responsive promoter) that mediate repression by RA were examined. Thus, various collagenase-CAT reporter plasmids together with RARα expression vectors were co-transfected into HeLa cells cultured in 10% serum in the absence (FIG. 8, black bars) or presence of RA (FIG. 8, striped bars).

FIG. 8 (bars 1–3) shows that addition of RA to HeLa cells resulted in about 6-fold repression of both 1200Col-CAT and 73Col-CAT reporter activity, whereas the activity of reporter plasmid 63Col-CAT remained unchanged.

These results indicate that repression is mediated by DNA sequences located between position –73 and –63 in the collagenase promoter. Thus, RAR, similar to GR, can inhibit induction of an AP-1 responsive promoter.

To further test the ability of RAR to inhibit induction of an AP-1 responsive promoter, the AP-1 inducible reporter construct (AP-1)$_5$-TKCAT was transfected into HeLa cells. The high basal activity of this promoter is also repressed in the presence of RA and RARα (FIG. 8, bar 4), whereas expression of the control TK promoter is not influenced by RA (FIG. 8, bars 5). As one might expect, the RA-responsive reporter βRE-TKCAT was activated in a hormone dependent manner (FIG. 8, bars 6).

The data shown in FIG. 8 demonstrate that repression of the collagenase promoter or heterologous reporter by RA depends on the presence of the AP-1 site.

EXAMPLE 8

RAR DNA Binding Domain and a Region Near the C-Terminus Are Necessary but Not Sufficient for Repression of Jun/AP-1 Activity The above experiments demonstrate that Jun/AP-1 activation can be efficiently repressed by RARα in a hormone dependent manner. To define regions of the receptor involved in repression, several RAR mutants were analyzed in co-transfection studies in CV-1 cells for their ability to repress (AP-1)$_5$-TKCAT reporter activity. In FIG. 9, the scale above each receptor indicates amino acid numbers. The wild type RARα consists of the N terminus (amino acids 1-80), the DNA binding domain (amino acids 81-153), and the ligand binding domain (amino acids 154-462). The deleted amino acids are indicated at left. RA dependent repression of 1200Col-CAT reporter activity obtained by co-transfection with 0.1 µg of RARα expression plasmids was set at 100%.

Deletion of the entire N terminus of RAR did not impair the ability of the receptor to repress CAT activity (FIG. 9, compare bar 1 with bar 2). Deletion of the DNA-binding domain, however, resulted in a complete loss of repression (FIG. 9, bar 3).

Further analysis revealed that a mutant in which the RARα DNA-binding domain had been swapped with that of the GR (RGR) was still able to fully repress (FIG. 9, bar 4). These results indicate that asteroid receptor DNA-binding domain is required for efficient repression. However, the target gene specificity of the DNA-binding domain is relatively unimportant.

Still further analyses revealed that both C-terminal truncation mutants 403* and 203* have completely lost the ability to repress (FIG. 9, bars 5 and 6). As another means to demonstrate the importance of the receptor ligand-binding domain, the C-terminus of RAR was exchanged with that of the oncogene v-erbA. The resulting mutant RRerbA also failed to repress (FIG. 9, bar 7).

EXAMPLE 9

Interferes with AP-1 Binding Activity

Figure 10:
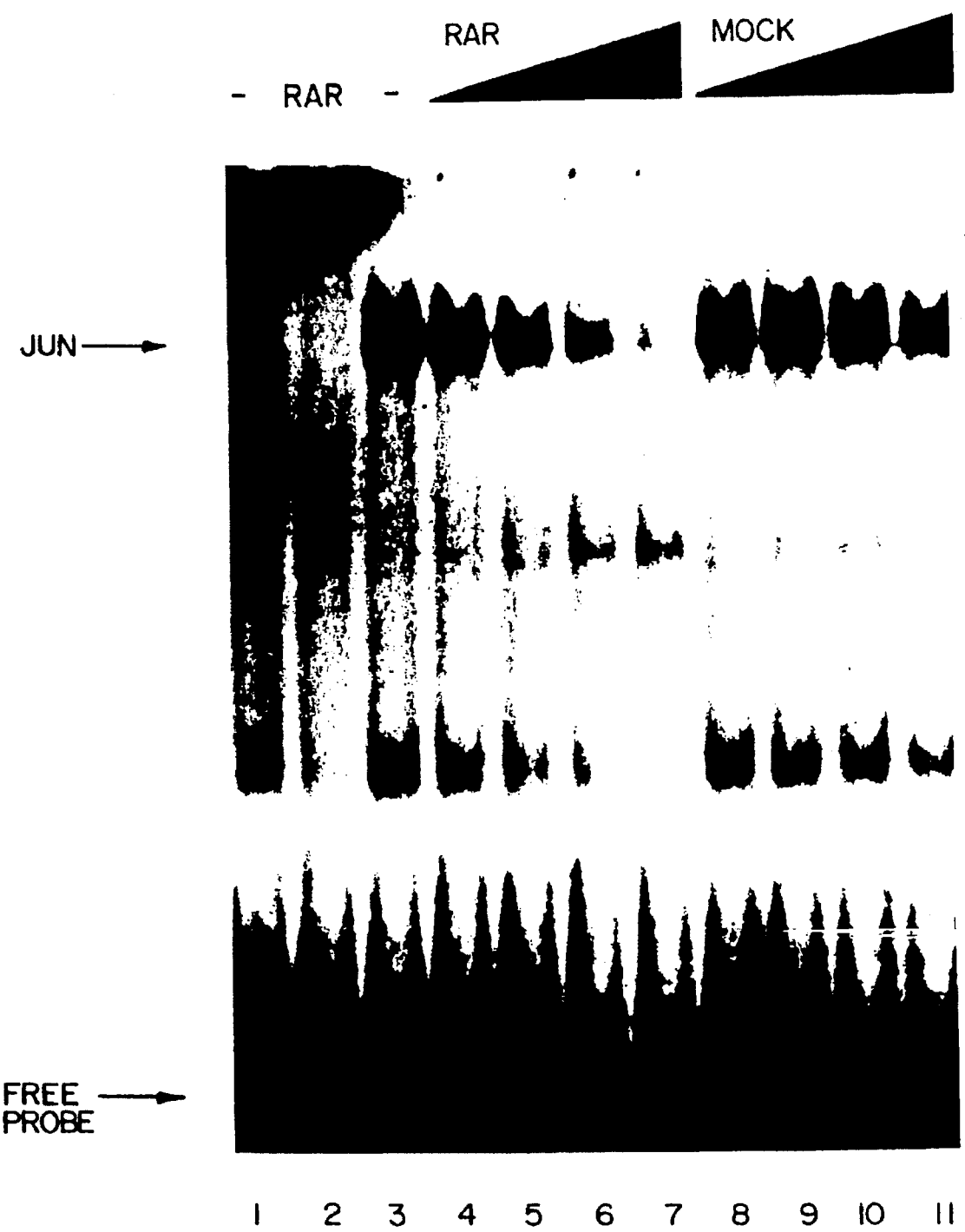
FIG. 10 presents gel retardation assays performed to determine the ability of RAR to repress the binding of c-Jun to an AP-1 binding site.

To test for a potential physical interactions between RAR and AP-1, gel retardation assays were performed. Bacterially expressed RARα was unable to form a retarded complex with a $^{32}$P-labeled oligonucleotide containing the collagenase AP-1 site (FIG. 10, lane 2), indicating that RAR does not inhibit collagenase expression by directly binding to this sequence. In contrast, in vitro translated c-Jun formed a specific, retarded complex (FIG. 10, lane 3). Addition of increased amounts of bacterially expressed RARα severely reduced the amount of complex formed in a dose-dependent fashion (FIG. 10, lanes 4-7), whereas mock-transformed BL21 bacterial lysate did not affect binding of c-Jun to DNA (FIG. 10, lanes 8-11).

Figure 11:
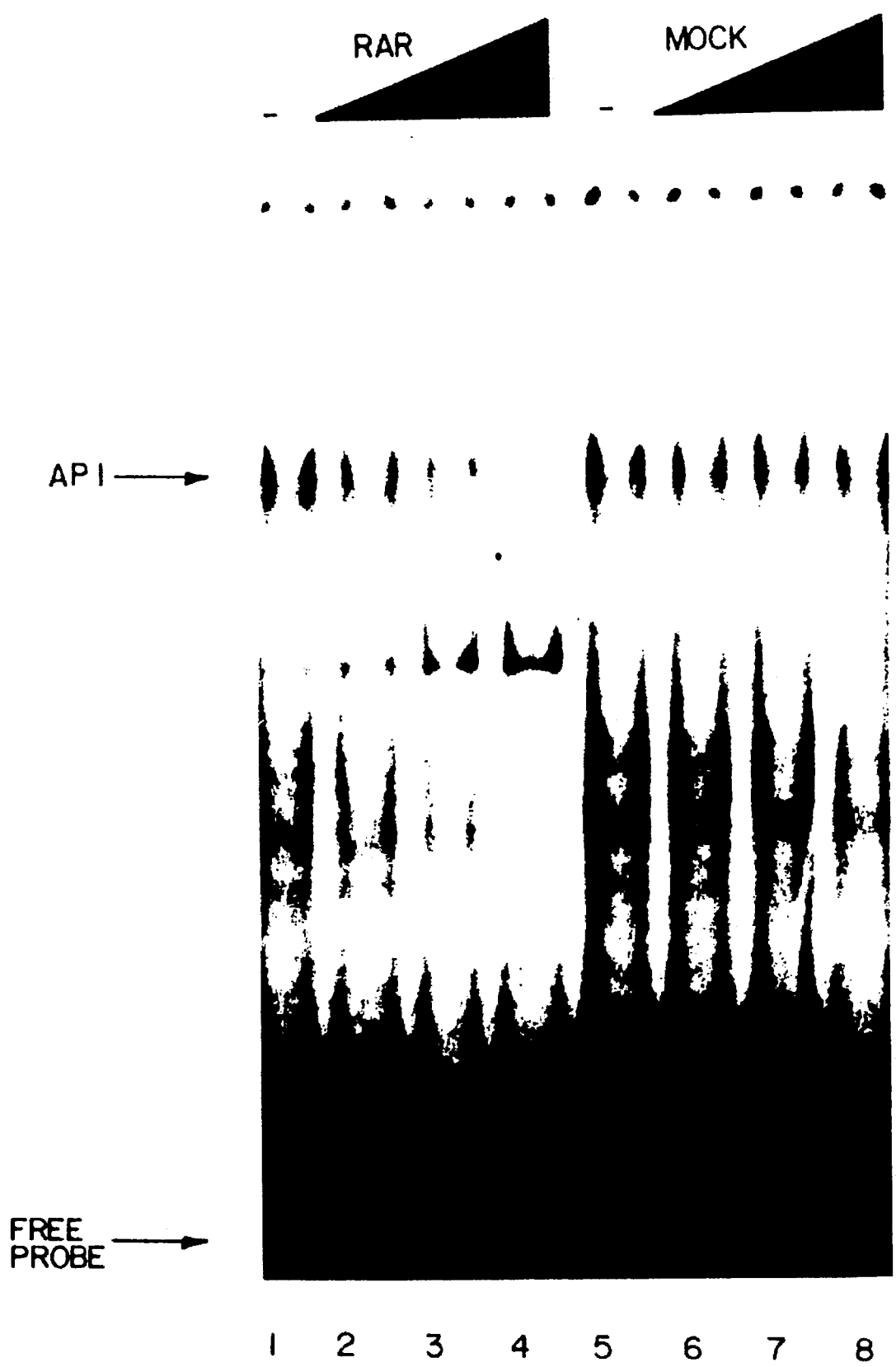
FIG. 11 presents gel retardation assays performed to investigate the ability of RAR to repress the binding of AP-1 to an AP-1 binding site.

Bacterially expressed RARα also inhibited AP-1 DNA binding when HeLa cell extract was used as AP-1 source (See FIG. 11, comparing lanes 1 with 2-4). Addition of mock-transformed BL21 bacterial lysate did not affect complex formation (FIG. 11, lanes 5-8). As a control, gel retardation assays were performed using NF-1 activity present in HeLa cell extracts and an oligonucleotide containing an NF-1 binding site. Addition of increasing amounts of bacterially expressed RARα had no effect on NF-1 binding activity, demonstrating the specificity of the inhibitory effect or RARα on AP-1 DNA binding.

The invention has been described in detail with particular reference to preferred embodiments thereof, but it will be understood that variations and modifications can be effected within the spirit and scope of the invention.

That which is claimed is:

1. A method for selecting a compound, said method comprising selecting a compound which disrupts the function of Activator Protein-1 (AP-1), as determined by a first assay system, but does not promote transcriptional activation of a steroid hormone responsive gene, as determined by a second assay system, wherein:

(a) said first assay system comprises a suitable growth medium and a cell line that expresses, in said suitable growth medium:
 (i) asteroid hormone receptor,
 (ii) AP-1, and
 (iii) an AP-1-responsive reporter;

(b) said determination by said first assay system comprises identifying a test compound which decreases expression of said AP-1-responsive reporter when said test compound is incubated in said first assay system, thereby identifying a compound which disrupts the function of AP-1;

(c) said second assay system comprises a second suitable growth medium and a cell line that expresses, in said second suitable growth medium:
 (i) asteroid hormone receptor,
 (ii) asteroid hormone-responsive reporter; and (d) said determination by said second assay system comprises identifying a test compound which does mot increase expression of said steroid hormone-responsive reporter when said test compound is incubated in said second assay system, thereby identifying a compound which does not promote transcriptional activation of asteroid hormone-responsive gene.

2. The method according to claim 1 wherein said compound forms a first complex with asteroid hormone receptor; wherein said first complex, in the presence of AP-1, disrupts the function of AP-1; and wherein said first complex is substantially unable to promote transcriptional activation of steroid hormone responsive genes.

3. The method according to claim 1 wherein said receptor is a glucocorticoid receptor, a retinoic acid receptor, a vitamin D$_3$ receptor, a thyroid receptor, a mineralocorticoid receptor, an estrogen receptor, an estrogen-related receptor, a retinoid receptor, an androgen receptor, or a progesterone receptor.

4. A method for identifying a compound which disrupts an Activator Protein-1 (AP-1) response pathway, but which exerts no substantial effect on asteroid hormone response pathway, said method comprising identifying a compound which has both an inhibitory effect on AP-1-responsive expression, as determined by a first assay system, and no substantial effect on steroid hormone-responsive expression, as determined by a second assay system, wherein:

(a) said first assay system comprises a suitable growth medium and a cell line that expresses, in said suitable growth medium:
 (i) asteroid hormone receptor,
 (ii) AP-1, and
 (iii) an AP-1-responsive reporter;

(b) said determination by said first assay system comprises identifying a test compound which decreases expression of said AP-1-responsive reporter when said test compound is incubated in said first assay system, thereby identifying a compound which inhibits AP-1-responsive expression;

(c) said second assay system comprises a second suitable growth medium and a cell line that expresses, in said second suitable growth medium:
 (i) asteroid hormone receptor,
 (ii) asteroid hormone-responsive reporter; and (d) said determination by said second assay system comprises identifying a test compound which does not increase expression of said steroid hormone-responsive reporter when said test compound is incubated in said second assay system, thereby identifying a compound which has no substantial effect on steroid hormone-responsive expression.

5. The method according to claim 4 wherein said receptor is a glucocorticoid receptor, a retinoic acid receptor, a vitamin $D_3$ receptor, a thyroid receptor, a mineralocorticoid receptor, an estrogen receptor, an estrogen-related receptor, a retinoid receptor, an androgen receptor or a progesterone receptor.

6. A method to repress transcription activation of a steroid hormone-responsive gene by steroid hormones in an expression system that expresses a steroid hormone-responsive gene, said method comprising:

exposing said system to compounds or conditions which induce Activator Protein-1 (AP-1) expression, wherein said AP-1 expression represses expression of said steroid hormone-responsive gene.

7. The method according to claim 6 wherein said steroid hormone-responsive gene is glucocorticoid-responsive, retinoic acid-responsive, vitamin $D_3$-responsive, thyroid hormone responsive, mineralocorticoid responsive, estrogen responsive, estrogen-related hormone responsive, androgen-responsive, progesterone-responsive, or retinoid-responsive.

8. The method according to claim 6 wherein said steroid hormone-responsive gene is glucocorticoid-responsive, thyroid hormone responsive, mineralocorticoid responsive, estrogen responsive, estrogen-related hormone responsive, androgen-responsive, progesterone-responsive, or retinoid-responsive.

9. The method according to claim 6 wherein said compounds or conditions which induce expression of AP-1 are compounds which induce tumor formation, growth factors, cytokines, neuropeptides, neurotransmitters, protein kinase c, or compounds which induce protein kinase c; or conditions of ultraviolet irradiation, gamma irradiation, stress or heat shock.

10. A method to repress transcription activation of a steroid hormone-responsive gene by steroid hormone compounds in an expression system that expresses a steroid hormone-responsive gene, said method comprising:

administering to said system a peptide comprising the leucine zipper region of c-Jun in an amount effective to repress expression of said steroid hormone-responsive gene.

11. The method according to claim 10 wherein the molar ratio of the leucine zipper region of c-Jun to steroid hormone receptor falls in the range of about 0.5:1 up to 100:1.

12. A method to repress transcription activation of an Activator Protein-1 (AP-1)-responsive gene by AP-1 in an expression system that expresses an AP-1-responsive gene, said method comprising:

administering to said system:
(a) a composition comprising:
(i) functional ligand-binding domain of steroid hormone receptor, and
(ii) functional DNA-binding domain of steroid hormone receptor, and
(b) a compound that binds to said ligand binding domain, in an amount effective to repress expression of said AP-1-responsive gene.

13. The method according to claim 12 wherein said AP-1-responsive gene is a collagenase gene, a c-Jun gene, a c-Fos gene, an immune-response gene, or a retinoic acid receptor-alpha gene.

14. The method according to claim 12 wherein said composition comprises functional domains of asteroid hormone receptor selected from the group consisting of a glucocorticoid receptor, a retinoic acid receptor, a vitamin $D_3$ receptor, a thyroid receptor, a mineralocorticoid receptor, an estrogen receptor, an estrogen-related receptor, a retinoid receptor, an androgen receptor and a progesterone receptor.

15. The method according to claim 12 wherein said composition comprises functional domains of asteroid hormone receptor selected from the group consisting of a glucocorticoid receptor, a thyroid receptor, a mineralocorticoid receptor, an estrogen receptor, an estrogen-related receptor, a retinoid receptor, an androgen receptor and a progesterone receptor.

16. The method according to claim 12 wherein the molar ratio, with respect to AP-1, of each of said ligand-binding domain or said DNA-binding domain in the composition falls in the range of about 0.5:1 up to 100:1.

17. A method to overcome the repression of expression of a gene product from a gene in an expression system having a steroid hormone present, when said gene is subject to negative regulation by steroid hormone receptors, said method comprising:

exposing said system to a compound or condition which induces Activator Protein-1 (AP-1) expression, wherein said AP-1 expression suppresses the repression of expression of said gene product.

18. The method according to claim 17 wherein said gene is a pro-opiomelanocortin gene, a prolactin gene, a proliferin gene, a chorionic gonadotropin alpha-subunit gene, a phosphoenolpyruvate carboxykinase gene, or a collagenase gene.

19. A method to overcome the inhibition of proliferation of cultured lymphoid cells by asteroid hormone in the presence of asteroid hormone receptor, said method comprising:

exposing said lymphoid cells to compounds or conditions which induce Activator Protein-1 (AP-1) expression, wherein said AP-1 expression suppresses the inhibition of proliferation of said lymphoid cells.

20. A method for selecting a compound which disrupts the function of Activator Protein-1 (AP-1), said method comprising:

1) incubating a test compound in an assay system comprising a suitable growth medium and a cell line that expresses, in said suitable growth medium:
   (i) steroid hormone receptor,
   (ii) AP-1, and
   (iii) AP-1-responsive reporter;
2) detecting AP-1 responsive reporter expression; and
3) selecting a compound which decreases expression of said AP-1 responsive reporter, thereby selecting a compound which disrupts the function of AP-1.

21. A method for selecting a compound which disrupts the function of Activator Protein-1 (AP-1), but does not affect the transcriptional activation of steroid hormone-responsive genes, said method comprising:

1) incubating a test compound which disrupts the function of AP-1 in an assay system comprising a suitable growth medium and a cell line that expresses, in said suitable growth medium:
   (i) steroid hormone receptor, and
   (ii) steroid hormone-responsive reporter; and
2) selecting a test compound which does not affect the transcriptional activation of steroid hormone-responsive genes, thereby selecting a compound which disrupts the function of Activator-Protein-1 (AP-1), but does not affect the transcriptional activation of steroid hormone-responsive genes.

22. A method to repress transcription activation of an Activator Protein-1 (AP-1)-responsive gene by AP-1 in an expression system that expresses an AP-1-responsive gone, said method comprising:

administering to said system:
(a) a composition comprising:
(i) functional ligand-binding domain of steroid hormone receptor, and
(ii) functional DNA-binding domain of steroid hormone receptor, in an amount effective to repress expression of said AP-1-responsive gene, wherein said system comprises an endogenous compound that binds to said ligand binding domain.

* * * * *